(12) United States Patent
Hasumura et al.

(10) Patent No.: US 11,291,649 B2
(45) Date of Patent: Apr. 5, 2022

(54) AMMONIA METABOLISM PROMOTER

(71) Applicant: Kao Corporation, Tokyo (JP)

(72) Inventors: Takahiro Hasumura, Utsunomiya (JP); Shu Chen, Maoka (JP); Noriyasu Ota, Shimotsuke (JP); Yoshihiko Minegishi, Utsunomiya (JP); Atsuko Otsuka, Haga-gun (JP); Akemi Kobayashi, Utsunomiya (JP)

(73) Assignee: Kao Corporation, Tokyo (JP)

( * ) Notice: Subject to any disclaimer, the term of this patent is extended or adjusted under 35 U.S.C. 154(b) by 74 days.

(21) Appl. No.: 16/619,701

(22) PCT Filed: May 18, 2018

(86) PCT No.: PCT/JP2018/019341
§ 371 (c)(1),
(2) Date: Dec. 5, 2019

(87) PCT Pub. No.: WO2018/225482
PCT Pub. Date: Dec. 13, 2018

(65) Prior Publication Data
US 2020/0197361 A1 Jun. 25, 2020

(30) Foreign Application Priority Data
Jun. 7, 2017 (JP) .............................. JP2017-112180

(51) Int. Cl.
| | |
|---|---|
| A61K 31/353 | (2006.01) |
| A23L 33/175 | (2016.01) |
| A23L 33/105 | (2016.01) |
| A61P 43/00 | (2006.01) |
| A61P 1/16 | (2006.01) |
| A61P 3/00 | (2006.01) |
| A61K 31/198 | (2006.01) |
| A61K 36/82 | (2006.01) |
| A61K 9/00 | (2006.01) |

(52) U.S. Cl.
CPC .......... *A61K 31/353* (2013.01); *A23L 33/105* (2016.08); *A23L 33/175* (2016.08); *A61K 31/198* (2013.01); *A61K 36/82* (2013.01); *A61P 1/16* (2018.01); *A61P 3/00* (2018.01); *A61P 43/00* (2018.01); *A61K 9/0053* (2013.01)

(58) Field of Classification Search
CPC ...... A61K 31/353; A61K 31/198; A61P 43/00
See application file for complete search history.

(56) References Cited

U.S. PATENT DOCUMENTS

| | | |
|---|---|---|
| 2009/0197944 A1 | 8/2009 | Ota et al. |
| 2009/0232917 A1 | 9/2009 | Komatsu et al. |
| 2010/0137226 A1 | 6/2010 | Komatsu et al. |
| 2010/0292332 A1 | 11/2010 | Ochiai et al. |
| 2012/0259016 A1 | 10/2012 | Jalan et al. |

FOREIGN PATENT DOCUMENTS

| | | |
|---|---|---|
| EP | 2 167 026 | 3/2010 |
| JP | 41-8592 B1 | 5/1966 |
| JP | 42-7767 B1 | 3/1967 |
| JP | 2000-239179 A | 9/2000 |
| JP | 2005-089384 A | 4/2005 |
| JP | 2007-330124 A | 12/2007 |
| JP | 2008-031148 A | 2/2008 |
| JP | 2011-132174 A | 7/2011 |
| JP | 2012-246294 A | 12/2012 |
| JP | 2013-060406 A | 4/2013 |
| JP | 2020-089318 A | 6/2020 |
| WO | WO 2006/056794 A | 6/2006 |
| WO | WO 2007/040244 A1 | 4/2007 |
| WO | WO 2007/142286 A1 | 12/2007 |
| WO | WO 2008/151994 A1 | 12/2008 |
| WO | WO 2009/048148 A1 | 4/2009 |

OTHER PUBLICATIONS

Extended European Search Report (EESR) including the supplementary European search report and the European search opinion, for EP application No. 18813630.3, dated Feb. 2, 2021.
(Continued)

*Primary Examiner* — Kevin E Weddington
(74) *Attorney, Agent, or Firm* — Sterne, Kessler, Goldstein & Fox P.L.L.C.

(57) ABSTRACT

A material which has excellent ammonia metabolism improving effect and is effective for endurance enhancement, anti-fatigue or the like is provided. An ammonia metabolism promoting agent, comprising catechins and ornithine as active ingredients. An endurance enhancing agent, comprising catechins and ornithine as active ingredients. An anti-fatigue agent, comprising catechins and ornithine as active ingredients. An agent for suppressing a reduction in blood glucose level by exercise, comprising catechins and ornithine as active ingredients. An agent for promoting recovery from reduced blood glucose level by exercise, comprising catechins and ornithine as active ingredients. An agent for suppressing a reduction in muscle glycogen by exercise, comprising catechins and ornithine as active ingredients. A muscle endurance enhancing agent, comprising catechins and ornithine as active ingredients. An agent for preventing or ameliorating hyperammonemia, hepatic encephalopathy or chronic fatigue syndrome, comprising catechins and ornithine as active ingredients.

3 Claims, 7 Drawing Sheets

(56) References Cited

OTHER PUBLICATIONS

International Search Report (ISR) for PCT/JP2018/019341; I.A. fd May 18, 2018, dated Aug. 21, 2018 from the Japan Patent Office, Tokyo, Japan.

International Preliminary Report on Patentability (IPRP), Chapter I of the Patent Cooperation Treaty, including the Written Opinion, for PCT/JP2018/019341; I.A. fd May 18, 2018, dated Dec. 10, 2019, by the International Bureau of WIPO, Geneva, Switzerland.

Takeda, K et al., "Effects of citrulline supplementation on fatigue and exercise performance in mice," J Nutr Sci Vitaminol (Tokyo). 2011;57(3):246-50.

Walker, V, "Ammonia toxicity and its prevention in inherited defects of the urea cycle," Diabetes Obes Metab. Sep. 2009;11(9):823-35. doi: 10.1111/j.1463-1326.2009.01054.x. Epub Jun. 16, 2009.

Meneguello, MO et al., "Effect of arginine, ornithine and citrulline supplementation upon performance and metabolism of trained rats," Cell Biochem Funct. Mar. 2003;21(1):85-91.

Sachdeva, AK et al., "Epigallocatechin gallate ameliorates behavioral and biochemical deficits in rat model of load-induced chronic fatigue syndrome," Brain Res Bull. Oct. 10, 2011;86(3-4):165-72. doi: 10.1016/j.brainresbull.2011.06.007. Epub Jul. 28, 2011.

Sachdeva, AK et al., "Protective effect of epigallocatechin gallate in murine water-immersion stress model of chronic fatigue syndrome," Basic Clin Pharmacol Toxicol. Jun. 2010;106(6):490-6. doi: 10.1111/j.1742-7843.2009.00525.x. Epub Jan. 18, 2010.

Sachdeva, AK et al., "Epigallocatechin gallate ameliorates chronic fatigue syndrome in mice: behavioral and biochemical evidence," Behav Brain Res. Dec. 28, 2009;205(2):414-20. doi: 10.1016/j.bbr.2009.07.020. Epub Jul. 28, 2009.

Tanaka, M et al., "Effects of (−)-epigallocatechin gallate in liver of an animal model of combined (physical and mental) fatigue,"Nutrition. Jun. 2008;24(6):599-603. doi: 10.1016/j.nut.2008.03.001.

[Figure 1]
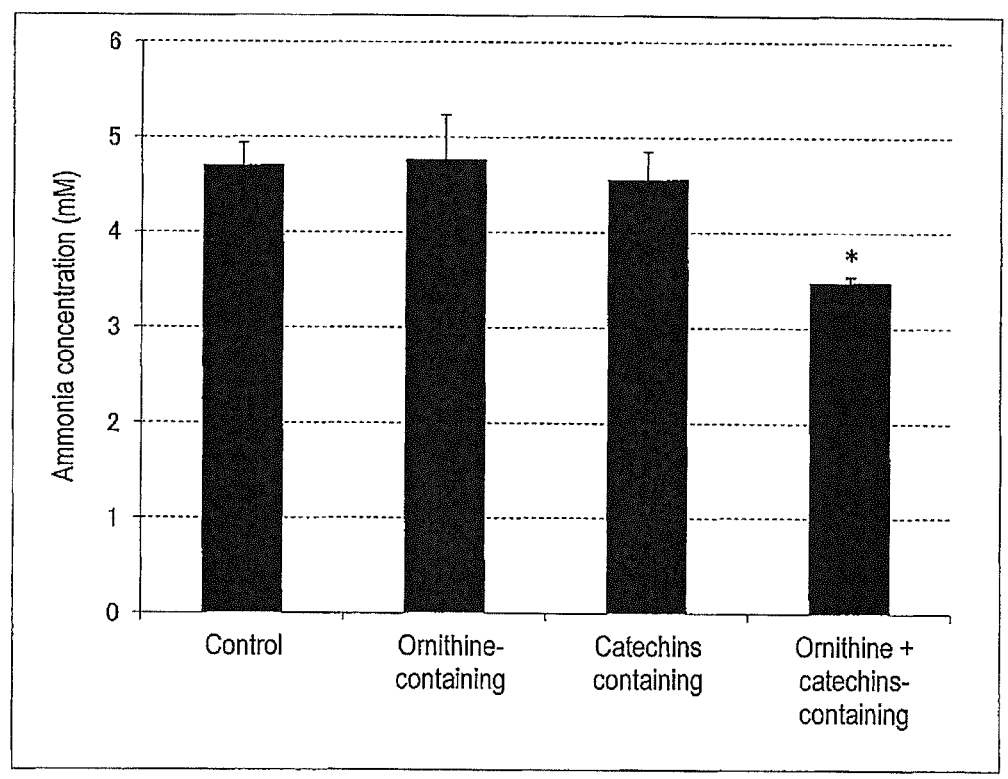

[Figure 2]
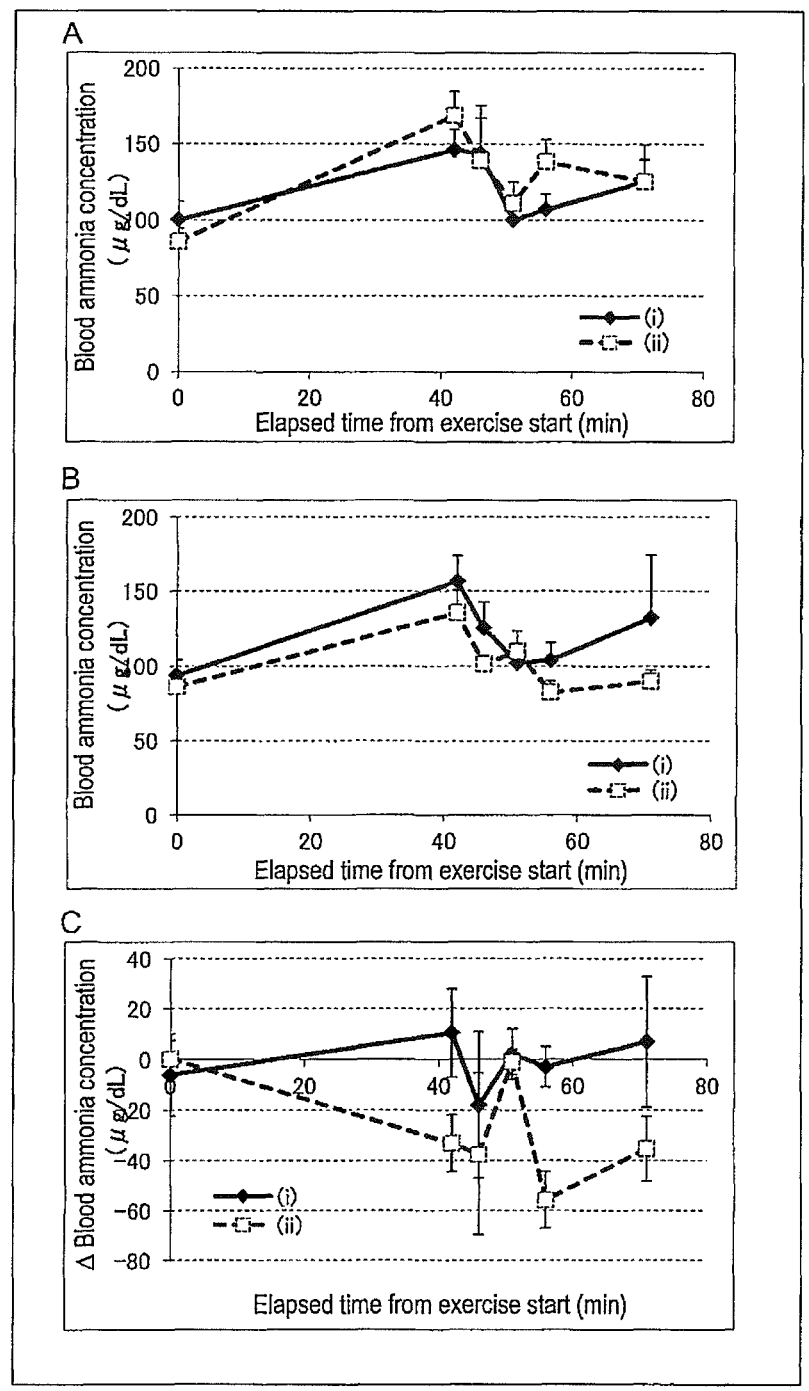

[Figure 3]
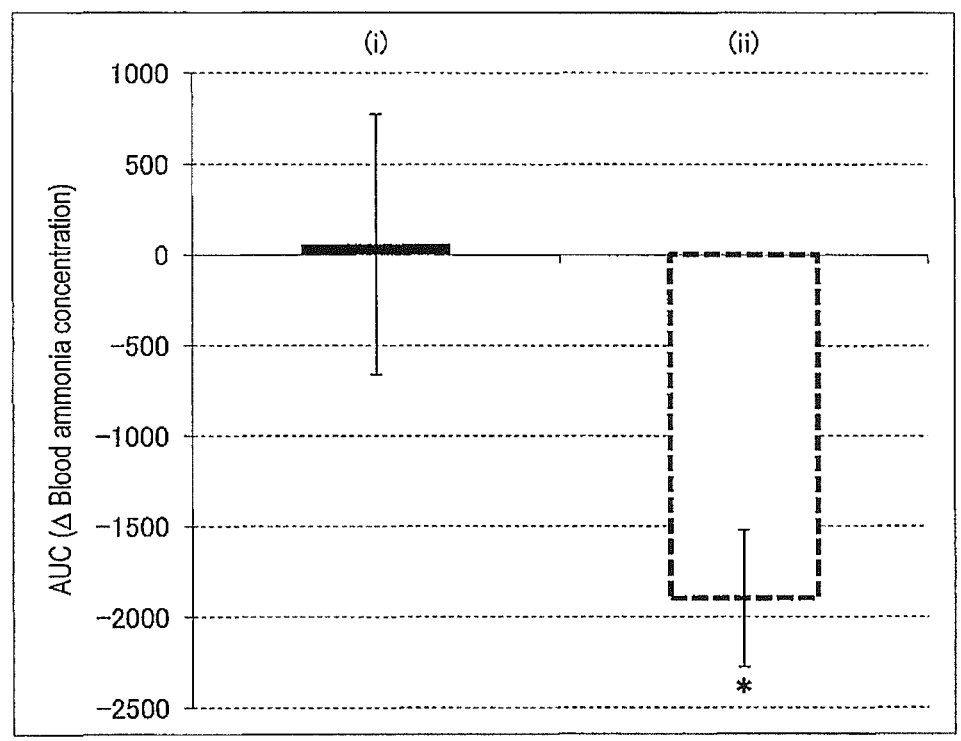

[Figure 4]
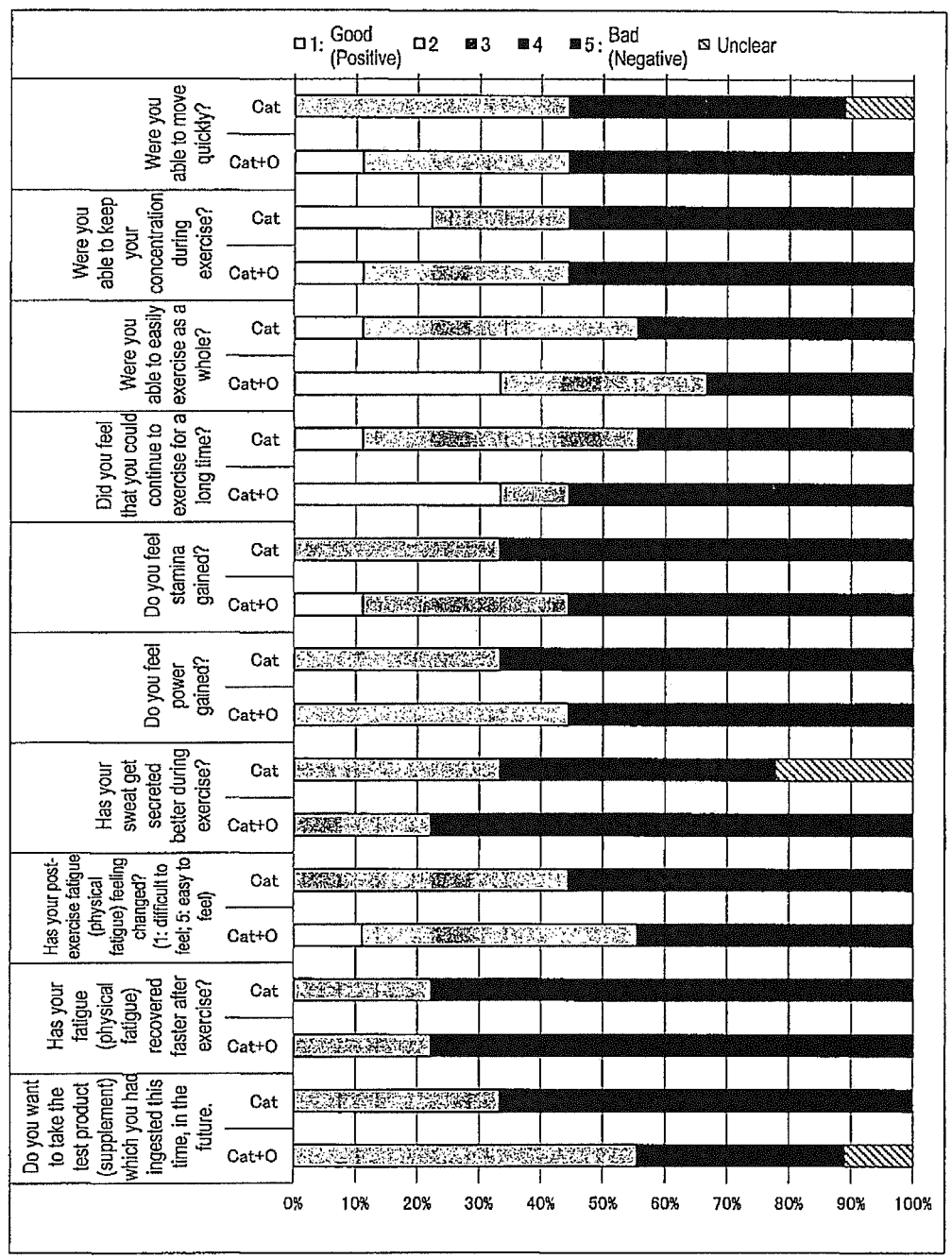

[Figure 5]
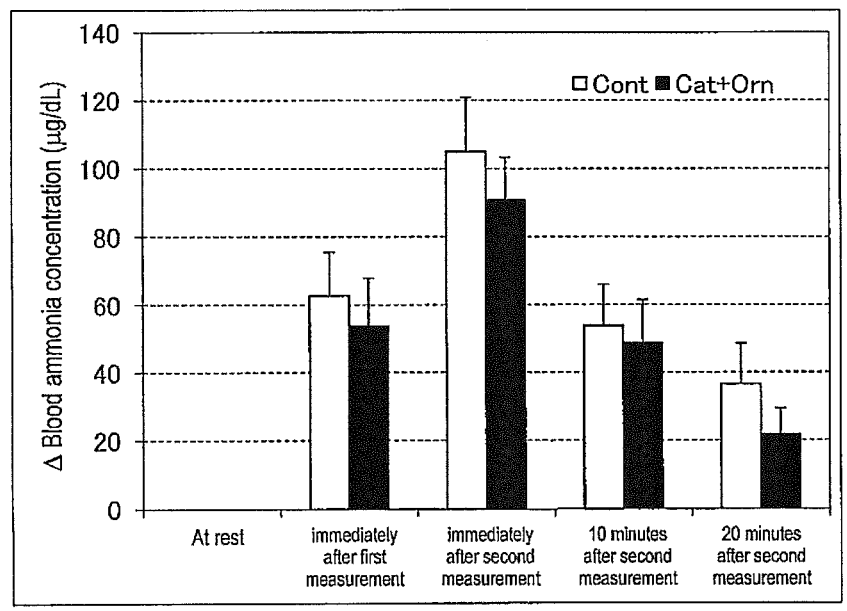
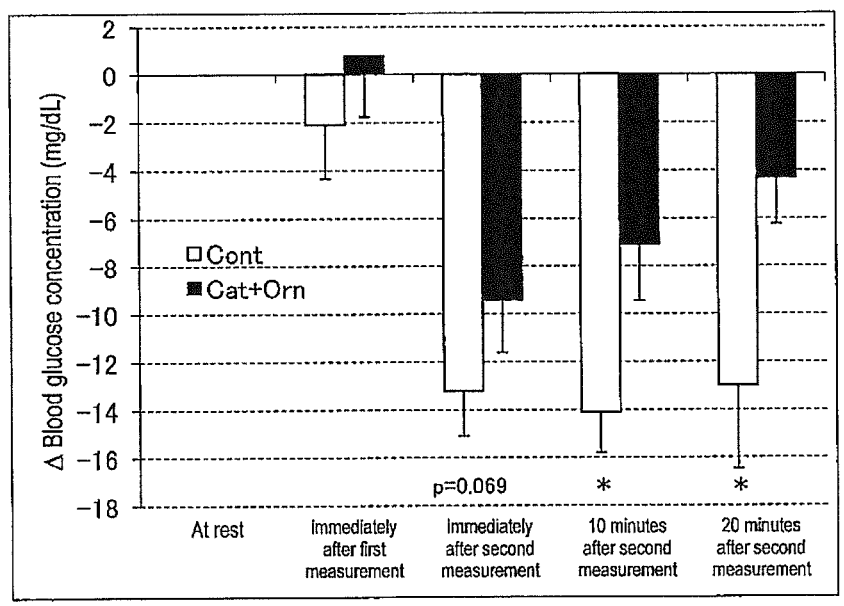

[Figure 6]
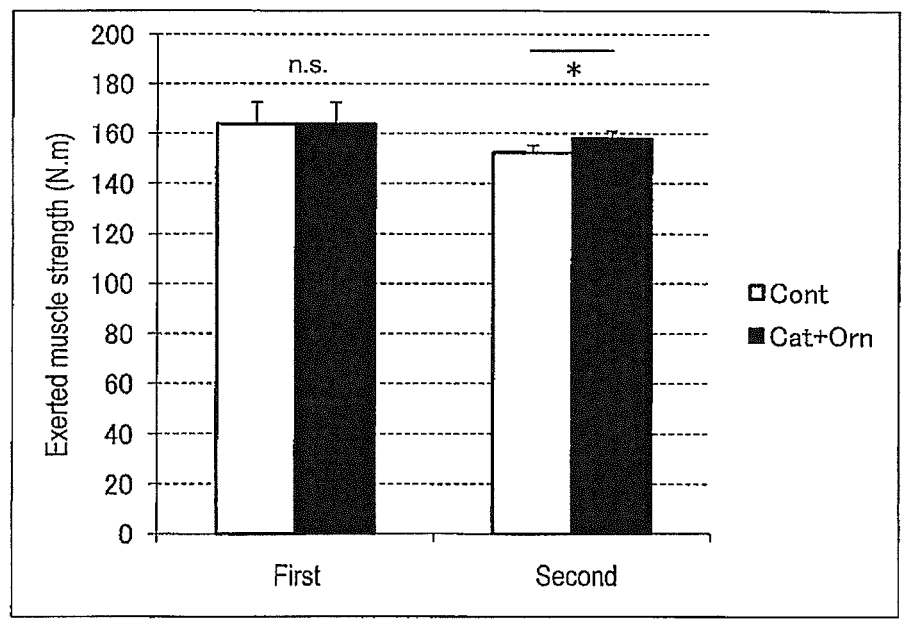
[Figure 7]
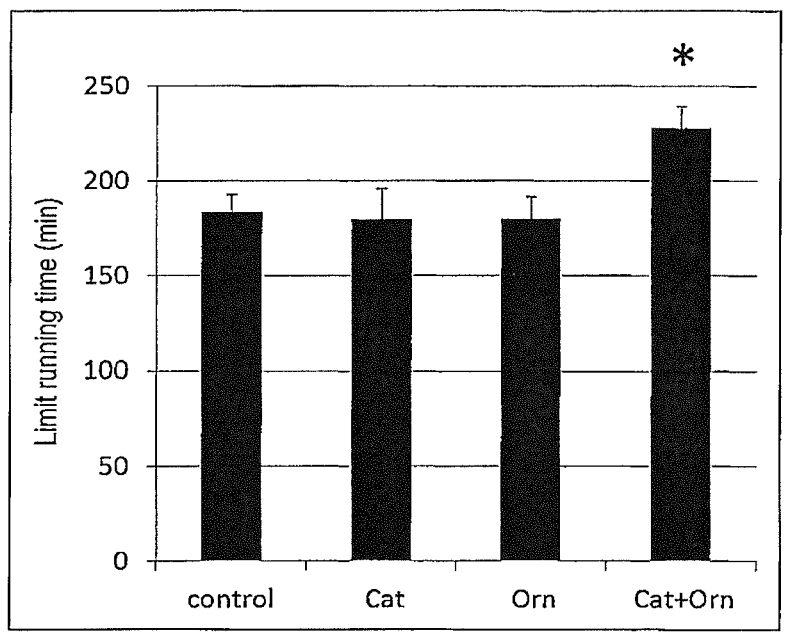

[Figure 8]
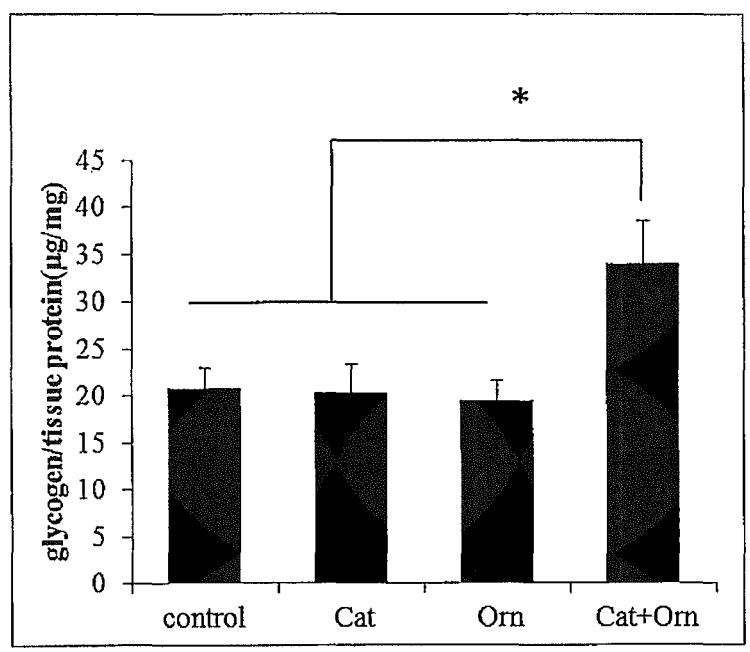

AMMONIA METABOLISM PROMOTER

FIELD OF THE INVENTION

The present invention relates to a material which promotes ammonia metabolism in the body and exerts an endurance enhancing effect and an anti-fatigue effect.

BACKGROUND OF THE INVENTION

Ammonia in the body is generated mainly in the process of protein metabolism or amino acid catabolism in muscle degradation by exercise or the like. Ammonia inhibits oxidation of pyruvate to acetyl-CoA to cause fatigue (see Non Patent Literature 1). It has also been known that ammonia causes nervous system hypofunction which is causative of central fatigue and promotes accumulation of lactic acid in muscles which leads to muscle fatigue (Patent Literature 1), and that hyperammonemia causes various disorders such as brain disorder (Non patent Literature 2). Ammonia accumulation in patients with chronic liver disease is thought to play an important role in the progression of hepatic encephalopathy and multiple organ failure (respiratory failure, cardiovascular failure and renal failure) (Patent Literature 2).

Ammonia in the body is converted to a harmless substance, urea by the urea cycle in the liver and excreted in the urine. Arginine, ornithine and citrulline are involved in the urea cycle in the liver which converts ammonia to a harmless substance, urea. It has been reported that the increase in blood ammonia is suppressed by ornithine, citrulline or arginine which is an amino acid involved in the urea cycle (Patent Literatures 3 and 4 and Non Patent Literature 1). In the body, citrulline is synthesized from ornithine, and citrulline is converted to arginine. It has been reported that ornithine suppresses the increase in blood ammonia and ameliorates fatigue (see Patent Literature 3). It has also been reported that ingestion of citrulline increases blood arginine and ameliorates brain fatigue (Patent Literatures 4 and 5).

Endurance is not only required in athletics, but is also essential for simple movements such as walking and running in our daily life and also for working in which muscular exertion is repeatedly performed. Reduced endurance causes difficulties in daily movements, especially in the elderly, and has a significant negative impact on quality of life (QOL). It is widely recognized that exercise training is effective in enhancing endurance. However, it is not easy at all to keep or enhance endurance by the exercise training due to the difficulty of securing time and keeping motivation and due to the risk of injury in the elderly.

Catechins have been previously reported as a component having an effect of enhancing endurance or preventing fatigue (Patent Literatures 6 and 7). However, there is no report on the effect of catechins on ammonia metabolism.

As components other than catechins, which have the effect of enhancing endurance or preventing fatigue, various amino acids such as ornithine (Patent Literature 3), citrulline (Non Patent Literature 1), combined use of citrulline and arginine (Patent Literature 4), combined use of arginine, ornithine and citrulline (Non Patent Literature 3) and the like have been reported.

(Patent Literature 1) JP-A-2000-239179
(Patent Literature 2) JP-A-2012-246294
(Patent Literature 3) JP-A-2011-132174
(Patent Literature 4) WO 2009/048148
(Patent Literature 5) JP-A-2013-060406
(Patent Literature 6) JP-A-2005-089384
(Patent Literature 7) JP-A-2008-031148
(Non Patent Literature 1) Takeda et al., J Nutr Sci Vitaminol, 2011, 57:246-250
(Non Patent Literature 2) Walker, Diabetes, Obesity and Metabolism, 2009, 11:823-835
(Non Patent Literature 3) Meneguello et al., Cell Biochem Funct, 2003, 21:85-91

SUMMARY OF THE INVENTION

The present invention provides an ammonia metabolism promoting agent comprising catechins and ornithine as active ingredients.

The present invention also provides an endurance enhancing agent comprising catechins and ornithine as active ingredients.

The present invention also provides an anti-fatigue agent comprising catechins and ornithine as active ingredients.

The present invention also provides an agent for suppressing a reduction in blood glucose level by exercise comprising catechins and ornithine as active ingredients.

The present invention also provides an agent for promoting recovery from reduced blood glucose level by exercise comprising catechins and ornithine as active ingredients.

The present invention also provides an agent for suppressing a reduction in muscle glycogen by exercise comprising catechins and ornithine as active ingredients.

The present invention also provides a muscle endurance enhancing agent comprising catechins and ornithine as active ingredients.

In addition, the present invention provides an ammonia metabolism promoting food comprising catechins and ornithine as active ingredients.

The present invention also provides an endurance enhancing food comprising catechins and ornithine as active ingredients.

The present invention also provides an anti-fatigue food comprising catechins and ornithine as active ingredients.

The present invention also provides a food for suppressing a reduction in blood glucose level by exercise comprising catechins and ornithine as active ingredients.

The present invention also provides a food for promoting recovery from reduced blood glucose level by exercise comprising catechins and ornithine as active ingredients.

The present invention also provides a food for suppressing a reduction in muscle glycogen by exercise comprising catechins and ornithine as active ingredients.

The present invention also provides a muscle endurance enhancing food comprising catechins and ornithine as active ingredients.

BRIEF DESCRIPTION OF THE DRAWINGS

FIG. 1 is a graph showing effects of catechins and ornithine on ammonia metabolism in the hepatocyte. The horizontal axis represents a type of hepatocyte culture medium, and the vertical axis represents an ammonia concentration in the medium. Each data is presented as mean±SE (n=3), *$p<0.05$ (Dunnett test, vs. a control group).

FIG. 2 shows graphs showing effects of catechins and ornithine on a blood ammonia concentration during exercise. A: a blood ammonia concentration after the first exercise (without ingestion of any test material); B: a blood ammonia concentration after the second exercise (after ingestion of a test material); and C: a Δ blood ammonia concentration ((a measured value at the second exercise)−(a measured value at the first exercise)). Each data is presented as mean±SE (n=9 per group).

FIG. 3 is a figure showing AUC of Δ blood ammonia concentration. Each data is presented as mean±SE (n=9 per group), *p<0.05 (t-test, vs. (i) group).

FIG. 4 is a diagram showing the results of questionnaire about the degree of fatigue.

FIG. 5 shows graphs showing (A) Δ blood ammonia concentration and (B) A glucose concentration, measured in a muscle endurance measuring test. At rest: before the first continuous muscle strength measurement; immediately after the first measurement: immediately after the first continuous muscle strength measurement; immediately after the second measurement: immediately after the second continuous muscle strength measurement; 10 minutes after the second measurement: 10 minutes after the second continuous muscle strength measurement; and 20 minutes after the second measurement: 20 minutes after the second continuous muscle strength measurement. Cont: a control group; and Cat+Orn: a combination group of catechins and ornithine. Each data is presented as mean±SE of measured values in 2 tests in a crossover test (n=9 per group). *p<0.05 (t-test, vs. control group).

FIG. 6 shows graphs showing an exerted muscle strength value measured in a muscle endurance measuring test. Cont: a control group; and Cat+Orn: a combination group of catechins and ornithine. Each data is presented as mean±SE of the exerted muscle strength values of both legs of all subjects measured in 2 tests (n=18 per group). *p<0.05 (ANOVA).

FIG. 7 is a graph showing a limit running time on a treadmill. Each data is presented as mean±SE (n=7 or 8), *p<0.05 (Dunnett test, vs. a control group).

FIG. 8 is a graph showing a muscle glycogen amount immediately after exercise in mice. Each data is presented as mean±SE (n=7 or 8), *p<0.05 (Tukey post hoc one way ANOVA).

DETAILED DESCRIPTION OF THE INVENTION

All Patent Literatures, Non Patent Literatures and other publications cited herein are hereby incorporated by reference in their entirety.

As used herein, "non-therapeutic" is a concept which does not include any medical practice, that is, does not include a method for surgery, medical treatment or diagnosis of a human, more specifically a method for surgery, medical treatment or diagnosis of a human by a doctor, or a medical professional or a person who has been instructed by a doctor.

As used herein, "prevention" refers to preventing, suppressing or delaying the onset of a disease or condition in an individual, or reducing the risk of onset of a disease or condition in an individual. As used herein, "amelioration" refers to a change for the better of a disease or condition; prevention, suppression or delay of deterioration of a disease or condition; or reversal, prevention, suppression or delay of progression of a disease or condition.

As used herein, "exercise" refers to physical exercise in a broad sense including, for example, sports, training, athletics such as aerobic exercise (exercise in a narrow sense), working with muscular exertion, daily movements or the like. As used herein, "exercise", when used with respect to an athlete or a person performing an exercise in a narrow sense, can preferably mean an exercise in a narrow sense, whereas "exercise", when used with respect to the middle-aged or older, the elderly, the valetudinarian, the sick or a person who is recovering from a disease, it may preferably mean working or daily movements with muscle exertion.

As used herein, "endurance" refers to the endurance for the "exercise" described above, and "endurance enhancement" is a concept including enhancement of endurance and suppression of a reduction in endurance. As used herein, "anti-fatigue" refers to suppressing fatigue caused by the "exercise" or promoting recovery from the fatigue.

As used herein, "muscle endurance" refers to the endurance of the skeletal muscle, that is, the ability of the skeletal muscle to exert its muscle strength continuously, and "muscle endurance enhancement" refers to the suppression of a reduction in muscle strength in situations in which the skeletal muscle is continuously driven. "Muscle endurance enhancement" also includes a condition in which a reduction in full exercise capacity is suppressed when repeating intermittent short periods of full exercise (such as dash, jump or spurt).

As used herein, "a reduction in blood glucose level by exercise" refers to a reduction in blood glucose due to an increase in glucose consumption by exercise, caused during exercise, immediately after interruption of exercise, or immediately after completion of exercise. As used herein, "recovery from reduced blood glucose level by exercise" refers to recovery of blood glucose level after interruption of exercise or after completion of exercise, from a condition in which blood glucose is reduced due to an increase in glucose consumption by exercise.

As used herein, "a reduction in muscle glycogen by exercise" refers to a reduction in glycogen storage in the muscle due to the consumption of muscle glycogen by muscle contraction activity. As used herein, "recovery from reduced muscle glycogen by exercise" refers to recovery of the muscle glycogen amount reduced by exercise, after discontinuation of exercise or after completion of exercise.

As used herein, "catechins" means at least one selected from the group consisting of catechin (C), gallocatechin (GC), catechin gallate (Cg), gallocatechin gallate (GCg), epicatechin (EC), epigallocatechin (EGC), epicatechin gallate (ECg) and epigallocatechin gallate (EGCg).

Catechins can be extracted, with water or hot water optionally with an extraction aid added, from tea leaves produced from leaves obtained from Camellia such as C. sinensis var. sinensis, C. sinensis var. assamica, Yabukita species or a hybrid thereof. The tea leaves include tea leaves of (1) green tea such as Sencha, Bancha, Gyokuro, Tencha or Kamairicha; (2) semi-fermented tea, collectively referred to as Oolong, such as Tieguanyin, Se Chung, Huangjin Gui or Wuyi tea; and (3) fermented tea, referred to as black tea, such as Darjeeling, Uva or Keemun. Extraction of catechins from the tea leaves can be performed by a conventional method such as extraction with stirring. An organic acid or organic acid salt such as sodium ascorbate may be previously added to the water or hot water for extraction. If necessary, extraction may be performed in combination with a method of extraction under so-called non-oxidative atmosphere while removing dissolved oxygen with degassing by boiling or with aeration of an inert gas such as nitrogen gas.

Alternatively, a concentrated or purified product of a tea extract may be used instead of extracting catechins directly from tea leaves. The concentrated product of a tea extract is, for example, a product obtained by concentrating an extract which is extracted from tea leaves with hot water or a water-soluble organic solvent, whereas the purified product of a tea extract is a product obtained by purifying the extract by using a solvent, a column or the like. Examples of the concentrated or purified product of a tea extract include products prepared by a method exemplified in detail in JP-A-59-219384, JP-A-4-20589, JP-A-5-260907, JP-A-5-

306279 or the like. The tea extract and the concentrated or purified product thereof to be used may be commercially available products. Examples of the commercially available product include "POLYPHENON" from Mitsui Norin Co., Ltd., "Teaflan" from ITO EN, LTD., "Sunphenone" from Taiyo Kagaku Co., Ltd. and "SunOolong" from Suntory Ltd. The concentrated or purified product of a tea extract may be in the form of solid, liquid, slurry, and those dissolved or diluted in water, carbonated water or a tea extract extracted by a usual procedure or the like, without being particularly limited thereto.

The catechins in the present invention may be also derived from other raw materials other than tea leaves, such as a grape and processed products thereof (such as wine or a juice) or from cocoa beans and processed products thereof, or may be a chemically synthesized product.

The catechins of the present invention is preferably used in the form of a concentrated or purified product of a tea extract, and more preferably in the form of a concentrated or purified product of a green tea extract.

In the present invention, ornithine can be used in the form of a free form or a salt thereof. Ornithine may be any of an L-form, a D-form, a DL-form and mixtures thereof, but is preferably an L-form.

Examples of the salt of ornithine include an acid addition salt, a metal salt, an ammonium salt, an organic amine addition salt and an amino acid addition salt. Examples of the acid addition salt include an inorganic acid salt such as a hydrochloride, a sulfate, a nitrate or a phosphate, and an organic salt such as an acetate, a maleate, a fumarate, a citrate, a malate, a lactate, an α-ketoglutarate, a gluconate and a caprylate. Examples of the metal salt include an alkali metal salt such as a sodium salt or a potassium salt; an alkaline-earth metal salt such as a magnesium salt and a calcium salt; an aluminum salt and a zinc salt. Examples of the ammonium salt include ammonium and tetramethylammonium salts. Examples of the organic amine addition salt include salts of morpholine and piperidine. Examples of the amino acid addition salt include salts of glycine, phenylalanine, lysine, aspartic acid and glutamic acid. Among them, preferable examples include a sodium salt and hydrochloride.

The free form of ornithine or a salt thereof can be obtained by a method of isolation and purification from animals and plants comprising them, chemical synthesis, fermentative production and the like. Alternatively, commercially available products may be purchased.

The present invention relates to the provision of a material, having an excellent ammonia metabolism promoting effect, which is effective for endurance enhancement, muscle endurance enhancement, suppression of a reduction in muscle glycogen or a reduction in blood glucose level by exercise, promotion of recovery from reduced muscle glycogen or reduced blood glucose level by exercise, and anti-fatigue.

The present inventors found that the combined use of catechins and ornithine remarkably enhances ammonia metabolism in hepatocytes as compared to catechins alone or ornithine alone. The present inventors also found that in an individual who has ingested a combination of catechins and ornithine, an increase in blood ammonia concentration and a reduction in blood glucose level and muscle glycogen during exercise are suppressed, and recovery of reduced blood glucose level by exercise is promoted, as well as endurance enhancement, muscle endurance enhancement and anti-fatigue effect are obtained.

The present invention promotes ammonia metabolism in the body, prevents a reduction in muscle glycogen or a reduction in blood glucose level by exercise, and provides alleviation of fatigue, endurance enhancement or muscle endurance enhancement. According to the present invention, in the valetudinarian or the middle-aged or older who suffers from reduced endurance and fatigue, in the elderly or in a person who needs enhancement in motor function (such as athletes), exercise endurance can be enhanced or fatigue by exercise can be alleviated.

In the present invention, by combined use of catechins and ornithine, remarkably higher ammonia metabolism promoting effect and endurance enhancing or anti-fatigue effect are achieved as compared to application of catechins or ornithine alone. In the present invention, by combined use of catechins and ornithine, an effect of suppressing a reduction in muscle glycogen or a reduction in blood glucose level by exercise, or an effect of promoting recovery of reduced muscle glycogen or reduced blood glucose level by exercise can be also obtained. In addition, in the present invention, by combined use of catechins and ornithine, muscle endurance promoting effect can be obtained. In the present invention, catechins and ornithine may be administered simultaneously as one composition comprising the two components or each component may be administered separately as long as they can cooperatively act in vivo.

Therefore, in one aspect, the present invention provides an ammonia metabolism promoting agent, comprising catechins and ornithine as active ingredients. The present invention also provides an endurance enhancing agent, comprising catechins and ornithine as active ingredients. The present invention also provides an anti-fatigue agent, comprising catechins and ornithine as active ingredients. The present invention also provides an agent for suppressing a reduction in blood glucose level by exercise, comprising catechins and ornithine as active ingredients. The present invention also provides an agent for promoting recovery from reduced blood glucose level by exercise, comprising catechins and ornithine as active ingredients. The present invention also provides a muscle endurance enhancing agent, comprising catechins and ornithine as active ingredients. The present invention also provides an agent for suppressing a reduction in muscle glycogen by exercise, comprising catechins and ornithine as active ingredients. The present invention also provides an agent for promoting recovery from reduced muscle glycogen by exercise, comprising catechins and ornithine as active ingredients.

In another aspect, the present invention provides use of catechins and ornithine for producing an ammonia metabolism promoting agent, an endurance enhancing agent, an anti-fatigue agent, an agent for suppressing a reduction in blood glucose level by exercise, an agent for promoting recovery from reduced blood glucose level by exercise, an agent for suppressing an reduction in muscle glycogen by exercise, an agent for promoting recovery from reduced muscle glycogen by exercise or a muscle endurance enhancing agent.

In one embodiment, the ammonia metabolism promoting agent, endurance enhancing agent, anti-fatigue agent, agent for suppressing a reduction in blood glucose level by exercise, agent for promoting recovery from reduced blood glucose level by exercise, agent for suppressing an reduction in muscle glycogen by exercise, agent for promoting recovery from reduced muscle glycogen by exercise or muscle endurance enhancing agent of the present invention is a composition comprising at least catechins and ornithine. In another embodiment, the agent of the present invention may be composed essentially of catechins and ornithine.

In another aspect, the present invention provides use of catechins and ornithine for promotion of ammonia metabolism, endurance enhancement, anti-fatigue, suppression of a reduction in blood glucose level by exercise, promotion of recovery from reduced blood glucose level by exercise, suppression of a reduction in muscle glycogen by exercise, promotion of recovery from reduced muscle glycogen by exercise, or muscle endurance enhancement. In a preferred embodiment, the catechins and ornithine are used in the form of a composition comprising them.

In further another embodiment, the present invention provides a combination of catechins and ornithine for use in promotion of ammonia metabolism, endurance enhancement, anti-fatigue, suppression of a reduction in blood glucose level by exercise, promotion of recovery from reduced blood glucose level by exercise, suppression of a reduction in muscle glycogen by exercise, promotion of recovery from reduced muscle glycogen by exercise, or muscle endurance enhancement. In a preferred embodiment, the combination of catechins and ornithine is a composition comprising them.

Examples of the composition comprising catechins and ornithine include the drugs and quasi drugs and the foods described later.

The use of catechins and ornithine according to the present invention may include therapeutic use and non-therapeutic use. Examples of the non-therapeutic use include administering or ingesting catechins and ornithine, not as a medical practice, but for the purpose of obtaining a health promotion effect such as alleviation of fatigue by physical activity in the daily life, endurance enhancement or fatigue alleviation in working with muscular exertion, endurance enhancement or muscle endurance enhancement during exercise in a narrow sense, or promotion of recovery from fatigue during or after exercise in a narrow sense. Examples of the non-therapeutic use also include the provision of catechins and ornithine, purporting to provide the above-described health promotion effect, in order to administer the catechins and ornithine to others or allow others to ingest the catechins and ornithine not as a medical practice.

Examples of the therapeutic use include application for the prevention or amelioration of diseases or conditions caused by excessive accumulation of ammonia, such as chronic fatigue syndrome, hyperammonemia and hepatic encephalopathy.

In the present invention, catechins and ornithine can be used for both human and non-human animals. Examples of the non-human animals include non-human mammals, amphibians and cartilaginous fish. Examples of the non-human mammals include apes, the other primates, mice, rats, horses, cattle, pigs, sheep, dogs, cats, hamsters and companion animals.

In another aspect, the present invention provides a method for promoting ammonia metabolism in a subject. The present invention also provides a method for enhancing endurance in the subject. The present invention also provides a method for anti-fatigue in a subject. The present invention also provides a method for suppressing a reduction in blood glucose level by exercise in a subject. The present invention also provides a method for promoting recovery from reduced blood glucose level by exercise in a subject. The present invention also provides a method for suppressing a reduction in muscle glycogen by exercise in a subject. The present invention also provides a method for promoting recovery from reduced muscle glycogen by exercise in a subject. The present invention also provides a method for enhancing muscle endurance in a subject. The present invention also provides a method for preventing or ameliorating of diseases or conditions caused by excessive accumulation of ammonia in a subject. The methods comprise administering effective amounts of catechins and ornithine to a subject. In a preferred embodiment, a composition comprising catechins and ornithine is administered. In another preferred embodiment, the administration is oral administration.

Examples of the subject to which the method of the present invention is applied include the above-described human and non-human animals in need of promotion of ammonia metabolism, endurance enhancement, anti-fatigue, suppression of a reduction in blood glucose level by exercise, promotion of recovery from reduced blood glucose level by exercise, suppression of a reduction in muscle glycogen by exercise, promotion of recovery from reduced muscle glycogen by exercise, or muscle endurance enhancement; and the above-described human and non-human animals in need of prevention or amelioration of diseases or conditions caused by excessive accumulation of ammonia, such as chronic fatigue syndrome, hyperammonemia or hepatic encephalopathy.

Further examples of the subject include the above-described human and non-human animals in need of alleviation of fatigue by physical activity in the daily life, endurance enhancement or fatigue alleviation in working with muscular exertion, endurance enhancement or muscle endurance enhancement during exercise in a narrow sense, or promotion of recovery from fatigue during or after exercise in a narrow sense, or the like.

Further examples of the subject include the above-described human and non-human animals in need of prevention or amelioration of a condition caused by hyperammonemia, such as respiratory alkalosis, slurred speech, tremors, weakness, increased or decreased muscle tone, ataxia, hypothermia, seizure, brain edema, coma, brain stem compression, confusion with headache, nausea, vomiting, agitation, delusions and delirium, irritability, aggression; hyperactive, bizarre or self-injurious behavior; cognitive deficits, protein aversion, anorexia or delayed growth, or the like.

Further examples of the subject include the above-described human and non-human animals in need of suppression of central fatigue associated with nervous system hypofunction caused by ammonia accumulation; and suppression of sleepiness or malaise caused by the central fatigue.

Further examples of the subject include the above-described human and non-human animals in need of prevention or amelioration of a symptom or condition associated with an increase in blood ammonia level, such as slurred speech, lack of motivation, coma, impaired consciousness, fuzzy vision, developmental disorder, protein-induced vomiting or poor suckling in infants.

Alternatively, the method for promoting ammonia metabolism of the present invention may be an in vitro method. Examples of the subject to which the in vitro method is applied can include liver tissues and cultured hepatocytes (such as primary cultured hepatocytes) derived from the above-described human or non-human animals.

The effective amount of administration in the method of the present invention can be an amount capable of achieving promotion of ammonia metabolism in a subject, or an amount capable of achieving endurance enhancement or anti-fatigue in a subject, or an amount capable of achieving suppression of a reduction in muscle glycogen or a reduction in blood glucose level by exercise or promotion of recovery from reduced muscle glycogen or a reduction in blood glucose level by exercise in a subject, or an amount capable of achieving muscle endurance enhancement in a subject. The ammonia metabolism level can be evaluated by measuring the blood ammonia concentration, the urea production amount, the ammonia concentration in a culture medium of hepatocytes, or the like with respect to a subject. The endurance and fatigue resistance can be evaluated by an exercise test such as a treadmill test or a bicycle pedaling test. The blood glucose level can be evaluated by a general glucometer. The amount of muscle glycogen can be evaluated by sampling skeletal muscles and extracting glycogen therefrom, and quantitatively determining the amount of glycogen in the extract using, for example, a kit intended therefor. The muscle endurance can be evaluated by a continuous muscle strength measuring test. In one embodiment, the effective amount may be an amount which statistically significantly increases the ammonia metabolism level in the group receiving catechins and ornithine as compared to the non-administration group. In another embodiment, the effective amount can be an amount which statistically significantly reduces the blood ammonia concentration in the population receiving catechins and ornithine as compared to the non-administration group. In another embodiment, the effective amount may be an amount which statistically significantly increases the blood glucose levels during or after exercise in the population receiving catechins and ornithine as compared to the non-administration group. In further another embodiment, the effective amount may be an amount which statistically significantly prolongs the exercise time in the population receiving catechins and ornithine as compared to the non-administration group. In further another embodiment, the effective amount may be an amount which statistically significantly suppresses a reduction in muscle strength accompanying exercise in the population receiving catechins and ornithine as compared to the non-administration group.

In the present invention, catechins and ornithine can be used as active ingredients for imparting, to a drug, a quasi drug or a food (including a food for non-human animals), a function such as promotion of ammonia metabolism, endurance enhancement, anti-fatigue, suppression of a reduction in blood glucose level by exercise, promotion of recovery from reduced blood glucose level by exercise, suppression of a reduction in muscle glycogen by exercise, promotion of recovery from reduced muscle glycogen by exercise, or muscle endurance enhancement; or as active ingredients for preventing or ameliorating diseases or conditions caused by excessive accumulation of ammonia, such as chronic fatigue syndrome, hyperammonemia or hepatic encephalopathy.

The drug (including quasi drug) is a drug for promotion of ammonia metabolism, endurance enhancement, anti-fatigue, suppression of a reduction in blood glucose level by exercise, promotion of recovery from reduced blood glucose level by exercise, suppression of a reduction in muscle glycogen by exercise, promotion of recovery from reduced muscle glycogen by exercise, or muscle endurance enhancement; or a drug for preventing or ameliorating diseases or conditions caused by excessive accumulation of ammonia, such as chronic fatigue syndrome, hyperammonemia or hepatic encephalopathy. The drug comprises catechins and ornithine as active ingredients for imparting the function. The drug may further comprise a pharmaceutically acceptable carrier, or another active ingredient, a pharmacological component or the like if necessary, as long as the functions of the active ingredients are not lost. The drug may be provided as one composition comprising catechins and ornithine, or may be provided as a combination of a plurality of compositions comprising catechins or ornithine.

The administration mode of the drug (including quasi drug) may be either an oral administration or a parenteral administration, but an oral administration is preferred. The dosage form of the drug is any dosage form which can be administered orally or parenterally, without being particularly limited thereto, such as an injection, a suppository, an inhalant, a transdermal agent, various topical agents, a tablet, a capsule, a granule, a powder, a solution or a syrup. The formulations in various dosage forms can be also prepared by appropriately combining catechins and ornithine with a pharmaceutically acceptable carrier (such as an excipient, a binder, a filler, a disintegrant, a surfactant, a lubricant, a dispersant, a buffer, a preservative, a flavoring agent, a perfume, a coating agent or a diluent), another pharmaceutically active ingredient and the like, according to a conventional method.

The food is a food for providing a function such as promotion of ammonia metabolism, endurance enhancement, anti-fatigue, suppression of a reduction in blood glucose level by exercise, promotion of recovery from reduced blood glucose level by exercise, suppression of a reduction in muscle glycogen by exercise, promotion of recovery from reduced muscle glycogen by exercise, or muscle endurance enhancement, and comprises catechins and ornithine as active ingredients for the function. The food includes a food for the sick as well as a food with health claims such as a food with nutrient function claims, a special health food or a food and drink with functional claims, which are based on the concept of promotion of ammonia metabolism, endurance enhancement, anti-fatigue, suppression of a reduction in blood glucose level by exercise, promotion of recovery from reduced blood glucose level by exercise, suppression of a reduction in muscle glycogen by exercise, promotion of recovery from reduced muscle glycogen by exercise, or muscle endurance enhancement, and on which the concept is indicated as needed.

The food provided by the present invention includes a drink. Therefore, "food" can be paraphrased into "food and drink". The food may be in the form of solid, semi-solid or liquid (such as a drink). Examples of the food include breads, noodles, rice, confectionaries such as cookies, jellies, dairy products, soups, frozen foods, instant foods, modified starch products, processed fish meat products, other processed foods, seasonings, nutritional supplements and drinks such as tea and coffee drinks, fruit drinks, carbonated drinks and jelly-like drinks, as well as ingredients thereof. Alternatively, the food may be a supplement in the form of an oral formulation such as a tablet, a capsule, a granule, a powder, a solution or a syrup. The food may be provided as one composition comprising catechins and ornithine, or may be provided as a combination of a plurality of compositions comprising catechins or ornithine.

The food can be prepared by appropriately combining catechins and ornithine with any food material or any additive which is acceptable in a food (such as a solvent, a softener, an oil, an emulsifier, a preservative, a flavor, a sweetener, a stabilizer, a coloring agent, an ultraviolet absorber, an antioxidant, a moisturizing agent, a thickener, an adhesive, a dispersing agent or a wetting agent), according to a conventional method.

The content of catechins in the drug (including quasi drug) is not particularly limited, but is preferably 0.1% by mass or more, more preferably 1% by mass or more and still more preferably 3% by mass or more, and preferably 20% by mass or less, more preferably 10% by mass or less and still more preferably 5% by mass or less. In addition, examples of the content include from 0.1 to 20% by mass, from 0.1 to 10% by mass, from 0.1 to 5% by mass, from 1 to 20% by mass, from 1 to 10% by mass, from 1 to 5% by mass, from 3 to 20% by mass, from 3 to 10% by mass and from 3 to 5% by mass.

The content of ornithine in the drug (including quasi drug) is not particularly limited, but is, in terms of free form of ornithine, preferably 0.3% by mass or more, more preferably 3% by mass or more, still more preferably 5% by mass or more and further preferably 9% by mass, and preferably 60% by mass or less, more preferably 30% by mass or less, still more preferably 20% by mass or less and further preferably 15% by mass or less. In addition, examples of the content include from 0.3 to 60% by mass, from 0.3 to 30% by mass, from 0.3 to 20% by mass, from 0.3 to 15% by mass, from 3 to 60% by mass, from 3 to 30% by mass, from 3 to 20% by mass, from 3 to 15% by mass, from 5 to 60% by mass, from 5 to 30% by mass, from 5 to 20% by mass, from 5 to 15% by mass, from 9 to 60% by mass, from 9 to 30% by mass, from 9 to 20% by mass and from 9 to 15% by mass.

In the drug (including quasi drug), any of the above-listed concentration of catechins (from 0.1 to 20% by mass, from 0.1 to 10% by mass, from 0.1 to 5% by mass, from 1 to 20% by mass, from 1 to 10% by mass, from 1 to 5% by mass, from 3 to 20% by mass, from 3 to 10% by mass and from 3 to 5% by mass) can be optionally combined with any of the above-listed concentration of ornithine (from 0.3 to 60% by mass, from 0.3 to 30% by mass, from 0.3 to 20% by mass, from 0.3 to 15% by mass, from 3 to 60% by mass, from 3 to 30% by mass, from 3 to 20% by mass, from 3 to 15% by mass, from 5 to 60% by mass, from 5 to 30% by mass, from 5 to 20% by mass, from 5 to 15% by mass, from 9 to 60% by mass, from 9 to 30% by mass, from 9 to 20% by mass and from 9 to 15% by mass).

The content of catechins in the food is not particularly limited, but is preferably 0.05% by mass or more, more preferably 0.1% by mass or more and still more preferably 1% by mass or more, and preferably 10% by mass or less, more preferably 5% by mass or less and further preferably 1% by mass or less. In addition, examples of the content include from 0.05 to 10% by mass, from 0.05 to 5% by mass, from 0.05 to 1% by mass, from 0.1 to 10% by mass, from 0.1 to 5% by mass, from 0.1 to 1% by mass, from 1 to 10% by mass and from 1 to 5% by mass.

The content of ornithine in the food is not particularly limited, but is, in terms of free form of ornithine, preferably 0.15% by mass or more, more preferably 0.3% by mass or more, still more preferably 3% by mass or more and further preferably 5% by mass or more, and preferably 30% by mass or less, more preferably 20% by mass or less, still more preferably 15% by mass or less, further preferably 5% by mass or less and still further preferably 3% by mass or less. In addition, examples of the content include from 0.15 to 30% by mass, from 0.15 to 20% by mass, from 0.15 to 15% by mass, from 0.15 to 5% by mass, from 0.15 to 3% by mass, from 0.3 to 30% by mass, from 0.3 to 20% by mass, from 0.3 to 15% by mass, from 0.3 to 5% by mass, from 0.3 to 3% by mass, from 3 to 30% by mass, from 3 to 20% by mass, from 3 to 15% by mass, from 3 to 5% by mass, from 5 to 30% by mass, from 5 to 20% by mass and from 5 to 15% by mass.

In the food, any of the above-listed concentration of catechins (from 0.05 to 10% by mass, from 0.05 to 5% by mass, from 0.05 to 1% by mass, from 0.1 to 10% by mass, from 0.1 to 5% by mass, from 0.1 to 1% by mass, from 1 to 10% by mass and from 1 to 5% by mass) can be optionally combined with any of the above-listed concentration of ornithine (from 0.15 to 30% by mass, from 0.15 to 20% by mass, from 0.15 to 15% by mass, from 0.15 to 5% by mass, from 0.15 to 3% by mass, from 0.3 to 20% by mass, from 0.3 to 30% by mass, from 0.3 to 15% by mass, from 0.3 to 5% by mass, from 0.3 to 3% by mass, from 3 to 30% by mass, from 3 to 20% by mass, from 3 to 15% by mass, from 3 to 5% by mass, from 5 to 30% by mass, from 5 to 20% by mass and from 5 to 15% by mass).

In the present invention, the dosages and dosing regimens of catechins and ornithine may be appropriately determined by those skilled in the art according to the species, body weight, sex, age, condition or other factors of the particular subject. When orally administered, examples of the daily dosages per adult of the catechins and ornithine according to the present invention are as follows without being limited to:

[catechins] preferably from 100 to 3,000 mg/60 kg body weight, more preferably from 250 to 2,000 mg/60 kg body weight, still more preferably from 250 to 1,000 mg/60 kg body weight and further preferably from 250 to 600 mg/60 kg body weight; and

[ornithine (in terms of free form)] preferably from 100 to 5,000 mg/60 kg body weight, more preferably from 250 to 3,000 mg/60 kg body weight, still more preferably from 400 to 2,000 mg/60 kg body weight, further preferably from 500 to 2,000 mg/60 kg body weight and still further preferably from 800 to 1,600 mg/60 kg body weight, or alternatively preferably from 250 to 800 mg/60 kg body weight and more preferably from 500 to 800 mg/60 kg body weight.

The above dosage is preferably administered once a day, or in divided doses twice or three or more times a day.

The mass ratio of catechins to ornithine (in terms of free form) used in the present invention is preferably from 1:0.1 to 1:10, more preferably from 1:0.5 to 1:10, still more preferably from 1:1 to 1:8, further preferably from 1:1 to 1:5 and still further preferably from 1:2 to 1:4. For example, the content ratio by mass of catechins to ornithine comprised in the ammonia metabolism promoting agent, endurance enhancing agent, anti-fatigue agent, an agent for suppressing a reduction in blood glucose level by exercise, an agent for promoting recovery from reduced blood glucose level by exercise, an agent for suppressing an reduction in muscle glycogen by exercise, an agent for promoting recovery from reduced muscle glycogen by exercise or muscle endurance enhancing agent of the present invention and an agent for preventing or ameliorating diseases or conditions caused by excessive accumulation of ammonia, of the present invention, is preferably from 1:0.1 to 1:10, more preferably from 1:0.5 to 1:10, still more preferably from 1:1 to 1:8, further preferably from 1:1 to 1:5 and still further preferably from 1:2 to 1:4. In addition, for example, the dosage ratio by mass of catechins to ornithine, both administered in a method for promoting ammonia metabolism, enhancing endurance, anti-fatigue, suppressing a reduction in blood glucose level by exercise, promoting recovery from reduced blood glucose level by exercise, suppressing a reduction in muscle glycogen by exercise, promoting recovery from reduced muscle glycogen by exercise, or enhancing muscle endurance, of the invention, and a method for preventing or ameliorating diseases or conditions caused by excessive accumulation of ammonia, of the present invention is preferably from 1:0.1 to 1:10, more preferably from 1:0.5 to 1:10, still more preferably from 1:1 to 1:8, further preferably from 1:1 to 1:5 and still further preferably from 1:2 to 1:4.

In a preferred embodiment of non-therapeutic use of catechins and ornithine for promotion of ammonia metabolism, endurance enhancement, anti-fatigue, suppression of a reduction in blood glucose level by exercise, promotion of recovery from reduced blood glucose level by exercise, suppression of a reduction in muscle glycogen by exercise, promotion of recovery from reduced muscle glycogen by exercise, or muscle endurance enhancement, according to the present invention, the catechins and ornithine are provided as a composition which comprises from 1 to 10% by mass of the catechins and from 5 to 20% by mass of ornithine (in terms of free form) and in which the mass ratio of the catechins to ornithine (in terms of free form) is from 1:0.5 to 1:10. The composition is preferably a food.

In a preferred embodiment of non-therapeutic use of catechins and ornithine for promotion of ammonia metabolism, endurance enhancement, anti-fatigue, suppression of a reduction in blood glucose level by exercise, promotion of recovery from reduced blood glucose level by exercise, suppression of a reduction in muscle glycogen by exercise, promotion of recovery from reduced muscle glycogen by exercise, or muscle endurance enhancement, according to the present invention, the catechins and ornithine are provided as a drink composition which comprises from 0.057 to 0.567% by mass of the catechins and from 0.283 to 1.132% by mass of ornithine (in terms of free form) and in which the mass ratio of the catechins to ornithine (in terms of free form) is from 1:0.5 to 1:10.

In a preferred embodiment of therapeutic use of catechins and ornithine for promotion of ammonia metabolism, endurance enhancement, anti-fatigue, suppression of a reduction in blood glucose level by exercise, promotion of recovery from reduced blood glucose level by exercise, suppression of a reduction in muscle glycogen by exercise, promotion of recovery from reduced muscle glycogen by exercise, or muscle endurance enhancement, or for preventing or ameliorating chronic fatigue syndrome, hyperammonemia or hepatic encephalopathy, according to the present invention, the catechins and ornithine are provided as a composition which comprises from 1 to 10% by mass of the catechins and from 5 to 20% by mass of ornithine (in terms of free form) and in which the mass ratio of the catechins to ornithine (in terms of free form) is from 1:0.5 to 1:10. The composition is preferably a drug.

In the present invention, a preferred example of the dosages of catechins and ornithine used for promotion of ammonia metabolism, endurance enhancement, anti-fatigue, suppression of a reduction in blood glucose level by exercise, promotion of recovery from reduced blood glucose level by exercise, suppression of a reduction in muscle glycogen by exercise, promotion of recovery from reduced muscle glycogen by exercise, or muscle endurance enhancement, or for preventing or ameliorating chronic fatigue syndrome, hyperammonemia or hepatic encephalopathy is from 250 to 1,000 mg/60 kg body weight of catechins and from 400 to 2,000 mg (in terms of free form)/60 kg body weight of ornithine as a daily oral dosage per adult. The above dosage is preferably administered once a day, or in divided doses twice or three or more times a day.

In the present invention, another material which has an ammonia metabolism promoting effect, an endurance enhancing effect, an anti-fatigue effect, an effect of suppressing a reduction in blood glucose level by exercise, an effect of promoting recovery from reduced blood glucose level by exercise, an effect of suppressing a reduction in muscle glycogen by exercise, an effect of promoting recovery of reduced muscle glycogen by exercise, or an effect of muscle endurance enhancement can be used as an active ingredient in combination of catechins and ornithine. Examples of another material include arginine, citrulline and a combination thereof.

The present invention also includes the following substances, production methods, uses, methods and the like as exemplary embodiments. However, the present invention is not limited to these embodiments.

[1] An ammonia metabolism promoting agent, comprising catechins and ornithine as active ingredients.
[2] An endurance enhancing agent, comprising catechins and ornithine as active ingredients.
[3] An anti-fatigue agent, comprising catechins and ornithine as active ingredients.
[4] An agent for suppressing a reduction in blood glucose level by exercise, comprising catechins and ornithine as active ingredients.
[5] An agent for promoting recovery from reduced blood glucose level by exercise, comprising catechins and ornithine as active ingredients.
[6] An agent for suppressing a reduction in muscle glycogen by exercise, comprising catechins and ornithine as active ingredients.
[7] An agent for promoting recovery from reduced muscle glycogen by exercise, comprising catechins and ornithine as active ingredients.
[8] A muscle endurance enhancing agent, comprising catechins and ornithine as active ingredients.
[9] An agent for preventing or ameliorating hyperammonemia, comprising catechins and ornithine as active ingredients.
[10] An agent for preventing or ameliorating hepatic encephalopathy, comprising catechins and ornithine as active ingredients.
[11] An agent for preventing or ameliorating chronic fatigue syndrome, comprising catechins and ornithine as active ingredients.
[12] The agent according to any one of [1] to [11], wherein the catechins is preferably at least one selected from the group consisting of catechin, gallocatechin, catechin gallate, gallocatechin gallate, epicatechin, epigallocatechin, epicatechin gallate and epigallocatechin gallate.
[13] The agent according to any one of [1] to [12], wherein preferably the agent is a drug or quasi drug and comprises from 0.1 to 20% by mass, from 0.1 to 10% by mass, from 0.1 to 5% by mass, from 1 to 20% by mass, from 1 to 10% by mass, from 1 to 5% by mass, from 3 to 20% by mass, from 3 to 10% by mass or from 3 to 5% by mass of the catechins.
[14] The agent according to [13], wherein the agent preferably comprises from 0.3 to 60% by mass, from 0.3 to 30% by mass, from 0.3 to 20% by mass, from 0.3 to 15% by mass, from 3 to 60% by mass, from 3 to 30% by mass, from 3 to 20% by mass, from 3 to 15% by mass, from 5 to 60% by mass, from 5 to 30% by mass, from 5 to 20% by mass, from 5 to 15% by mass, from 9 to 60% by mass, from 9 to 30% by mass, from 9 to 20% by mass or from 9 to 15% by mass of the ornithine.
[15] The agent according to any one of [1] to [12], wherein preferably the agent is a food and comprises from 0.05 to 10% by mass, from 0.05 to 5% by mass, from 0.05 to 1% by mass, from 0.1 to 10% by mass, from 0.1 to 5% by mass, from 0.1 to 1% by mass, from 1 to 10% by mass or from 1 to 5% by mass of the catechins.
[16] The agent according to [15], wherein the agent preferably comprises from 0.15 to 30% by mass, from 0.15 to 20% by mass, from 0.15 to 15% by mass, from 0.15 to 5% by mass, from 0.15 to 3% by mass, from 0.3 to 30% by mass, from 0.3 to 20% by mass, from 0.3 to 15% by mass, from 0.3 to 5% by mass, from 0.3 to 3% by mass, from 3 to 30% by mass, from 3 to 20% by mass, from 3 to 15% by mass, from 3 to 5% by mass, from 5 to 30% by mass, from 5 to 20% by mass or from 5 to 15% by mass of the ornithine.

[17] The agent according to any one of [1] to [16], wherein the mass ratio of the catechins to the ornithine is preferably from 1:0.1 to 1:10, more preferably from 1:0.5 to 1:10, still more preferably from 1:1 to 1:8, further preferably from 1:1 to 1:5 and still further preferably from 1:2 to 1:4.

[18] The agent according to any one of [1] to [17], wherein the agent is an oral formulation.

[19] Use of catechins and ornithine for producing an ammonia metabolism promoting agent.

[20] Use of catechins and ornithine for producing an endurance enhancing agent.

[21] Use of catechins and ornithine for producing an anti-fatigue agent.

[22] Use of a catechins and ornithine for producing an agent for suppressing a reduction in blood glucose level by exercise.

[23] Use of catechins and ornithine for producing an agent for promoting recovery from reduced blood glucose level by exercise.

[24] Use of catechins and ornithine for producing an agent for suppressing a reduction in muscle glycogen by exercise.

[25] Use of catechins and ornithine for producing an agent for promoting recovery from reduced muscle glycogen by exercise.

[26] Use of catechins and ornithine for producing a muscle endurance enhancing agent.

[27] Use of catechins and ornithine for producing an agent for preventing or ameliorating hyperammonemia.

[28] Use of catechins and ornithine for producing an agent for preventing or ameliorating hepatic encephalopathy.

[29] Use of catechins and ornithine for producing an agent for preventing or ameliorating chronic fatigue syndrome.

[30] The use according to any one of [19] to [29], wherein the catechins is preferably at least one selected from the group consisting of catechin, gallocatechin, catechin gallate, gallocatechin gallate, epicatechin, epigallocatechin, epicatechin gallate and epigallocatechin gallate.

[31] The use according to any one of [19] to [30], wherein preferably the agent is a drug or quasi drug and comprises from 0.1 to 20% by mass, from 0.1 to 10% by mass, from 0.1 to 5% by mass, from 1 to 20% by mass, from 1 to 10% by mass, from 1 to 5% by mass, from 3 to 20% by mass, from 3 to 10% by mass or from 3 to 5% by mass of the catechins.

[32] The use according to [31], wherein the agent preferably comprises from 0.3 to 60% by mass, from 0.3 to 30% by mass, from 0.3 to 20% by mass, from 0.3 to 15% by mass, from 3 to 60% by mass, from 3 to 30% by mass, from 3 to 20% by mass, from 3 to 15% by mass, from 5 to 60% by mass, from 5 to 30% by mass, from 5 to 20% by mass, from 5 to 15% by mass, from 9 to 60% by mass, from 9 to 30% by mass, from 9 to 20% by mass or from 9 to 15% by mass of the ornithine.

[33] The use according to any one of [19] to [30], wherein preferably the agent is a food and comprises from 0.05 to 10% by mass, from 0.05 to 5% by mass, from 0.05 to 1% by mass, from 0.1 to 10% by mass, from 0.1 to 5% by mass, from 0.1 to 1% by mass, from 1 to 10% by mass or from 1 to 5% by mass of the catechins.

[34] The use according to [33], wherein the agent preferably comprises from 0.15 to 30% by mass, from 0.15 to 20% by mass, from 0.15 to 15% by mass, from 0.15 to 5% by mass, from 0.15 to 3% by mass, from 0.3 to 30% by mass, from 0.3 to 20% by mass, from 0.3 to 15% by mass, from 0.3 to 5% by mass, from 0.3 to 3% by mass, from 3 to 30% by mass, from 3 to 20% by mass, from 3 to 15% by mass, from 3 to 5% by mass, from 5 to 30% by mass, from 5 to 20% by mass or from 5 to 15% by mass of the ornithine.

[35] The use according to any one of [19] to [34], wherein the mass ratio of the catechins to the ornithine is preferably from 1:0.1 to 1:10, more preferably from 1:0.5 to 1:10, still more preferably from 1:1 to 1:8, further preferably from 1:1 to 1:5 and still further preferably from 1:2 to 1:4.

[36] The use according to any one of [19] to [35], wherein the agent is an oral formulation.

[37] Use of catechins and ornithine for promotion of ammonia metabolism.

[38] Use of catechins and ornithine for endurance enhancement.

[39] Use of catechins and ornithine for anti-fatigue.

[40] Use of catechins and ornithine for suppression of a reduction in blood glucose level by exercise.

[41] Use of catechins and ornithine for promotion of recovery from reduced blood glucose level by exercise.

[42] Use of catechins and ornithine for suppression of a reduction in muscle glycogen by exercise.

[43] Use of catechins and ornithine for promotion of recovery from reduced muscle glycogen by exercise.

[44] Use of catechins and ornithine for muscle endurance enhancement.

[45] Use of catechins and ornithine for preventing or ameliorating hyperammonemia.

[46] Use of catechins and ornithine for preventing or ameliorating hepatic encephalopathy.

[47] Use of catechins and ornithine for preventing or ameliorating chronic fatigue syndrome.

[48] The use according to any one of [37] to [47], wherein the catechins is preferably at least one selected from the group consisting of catechin, gallocatechin, catechin gallate, gallocatechin gallate, epicatechin, epigallocatechin, epicatechin gallate and epigallocatechin gallate.

[49] The use according to any one of [37] to [48], wherein the catechins and ornithine are preferably used in the form of a drug or quasi drug comprising from 0.1 to 20% by mass, from 0.1 to 10% by mass, from 0.1 to 5% by mass, from 1 to 20% by mass, from 1 to 10% by mass, from 1 to 5% by mass, from 3 to 20% by mass, from 3 to 10% by mass or from 3 to 5% by mass of the catechins.

[50] The use according to [49], wherein the drug or quasi drug preferably comprises from 0.3 to 60% by mass, from 0.3 to 30% by mass, from 0.3 to 20% by mass, from 0.3 to 15% by mass, from 3 to 60% by mass, from 3 to 30% by mass, from 3 to 20% by mass, from 3 to 15% by mass, from 5 to 60% by mass, from 5 to 30% by mass, from 5 to 20% by mass, from 5 to 15% by mass, from 9 to 60% by mass, from 9 to 30% by mass, from 9 to 20% by mass or from 9 to 15% by mass of the ornithine.

[51] The use according to any one of [37] to [48], wherein the catechins and ornithine are preferably used in the form of a food comprising from 0.05 to 10% by mass, from 0.05 to 5% by mass, from 0.05 to 1% by mass, from 0.1 to 10% by mass, from 0.1 to 5% by mass, from 0.1 to 1% by mass, from 1 to 10% by mass or from 1 to 5% by mass of the catechins.

[52] The use according to [51], wherein the food preferably comprises from 0.15 to 30% by mass, from 0.15 to 20% by mass, from 0.15 to 15% by mass, from 0.15 to 5% by mass, from 0.15 to 3% by mass, from 0.3 to 30% by mass, from 0.3 to 20% by mass, from 0.3 to 15% by mass, from 0.3 to 5% by mass, from 0.3 to 3% by mass, from 3 to 30% by mass, from 3 to 20% by mass, from 3 to 15% by mass, from 3 to 5% by mass, from 5 to 30% by mass, from 5 to 20% by mass or from 5 to 15% by mass of the ornithine.

[53] The use according to any one of [37] to [52], wherein the mass ratio of the catechins to the ornithine is preferably from 1:0.1 to 1:10, more preferably from 1:0.5 to 1:10, still more preferably from 1:1 to 1:8, further preferably from 1:1 to 1:5 and still further preferably from 1:2 to 1:4.

[54] The use according to any one of [37] to [53], wherein the catechins and ornithine are preferably orally administered.

[55] A combination of catechins and ornithine for use in promotion of ammonia metabolism.

[56] A combination of catechins and ornithine for use in endurance enhancement.

[57] A combination of catechins and ornithine for use in anti-fatigue.

[58] A combination of catechins and ornithine for use in suppression of a reduction in blood glucose level by exercise.

[59] A combination of catechins and ornithine for use in promotion of recovery from reduced blood glucose level by exercise.

[60] A combination of catechins and ornithine for use in suppression of a reduction in muscle glycogen by exercise.

[61] A combination of catechins and ornithine for use in promotion of recovery from reduced muscle glycogen by exercise.

[62] A combination of catechins and ornithine for use in muscle endurance enhancement.

[63] A combination of catechins and ornithine for use in preventing or ameliorating hyperammonemia.

[64] A combination of catechins and ornithine for use in preventing or ameliorating hepatic encephalopathy.

[65] A combination of catechins and ornithine for use in preventing or ameliorating chronic fatigue syndrome.

[66] The combination of catechins and ornithine according to any one of [55] to [65], wherein the catechins is preferably at least one selected from the group consisting of catechin, gallocatechin, catechin gallate, gallocatechin gallate, epicatechin, epigallocatechin, epicatechin gallate and epigallocatechin gallate.

[67] The combination of catechins and ornithine according to any one of [55] to [66], which is preferably a drug or quasi drug comprising from 0.1 to 20% by mass, from 0.1 to 10% by mass, from 0.1 to 5% by mass, from 1 to 20% by mass, from 1 to 10% by mass, from 1 to 5% by mass, from 3 to 20% by mass, from 3 to 10% by mass or from 3 to 5% by mass of the catechins.

[68] The combination of catechins and ornithine according to [67], wherein the drug or quasi drug preferably comprises from 0.3 to 60% by mass, from 0.3 to 30% by mass, from 0.3 to 20% by mass, from 0.3 to 15% by mass, from 3 to 60% by mass, from 3 to 30% by mass, from 3 to 20% by mass, from 3 to 15% by mass, from 5 to 60% by mass, from 5 to 30% by mass, from 5 to 20% by mass, from 5 to 15% by mass, from 9 to 60% by mass, from 9 to 30% by mass, from 9 to 20% by mass or from 9 to 15% by mass of the ornithine.

[69] The combination of catechins and ornithine according to any one of [55] to [66], which is preferably a food comprising from 0.05 to 10% by mass, from 0.05 to 5% by mass, from 0.05 to 1% by mass, from 0.1 to 10% by mass, from 0.1 to 5% by mass, from 0.1 to 1% by mass, from 1 to 10% by mass or from 1 to 5% by mass of the catechins.

[70] The combination of catechins and ornithine according to [69], wherein the food preferably comprises from 0.15 to 30% by mass, from 0.15 to 20% by mass, from 0.15 to 15% by mass, from 0.15 to 5% by mass, from 0.15 to 3% by mass, from 0.3 to 30% by mass, from 0.3 to 20% by mass, from 0.3 to 15% by mass, from 0.3 to 5% by mass, from 0.3 to 3% by mass, from 3 to 30% by mass, from 3 to 20% by mass, from 3 to 15% by mass, from 3 to 5% by mass, from 5 to 30% by mass, from 5 to 20% by mass or from 5 to 15% by mass of the ornithine.

[71] The combination of catechins and ornithine according to any one of [55] to [70], wherein the mass ratio of the catechins to the ornithine is preferably from 1:0.1 to 1:10, more preferably from 1:0.5 to 1:10, still more preferably from 1:1 to 1:8, further preferably from 1:1 to 1:5 and still further preferably from 1:2 to 1:4.

[72] The combination of catechins and ornithine according to any one of [55] to [71], which is preferably orally administered.

[73] The combination of catechins and ornithine according to any one of [55] to [72], wherein the daily dosages per adult of the catechins and ornithine are as follows:

[catechins] preferably from 100 to 3,000 mg/60 kg body weight, more preferably from 250 to 2,000 mg/60 kg body weight, still more preferably from 250 to 1,000 mg/60 kg body weight and further preferably from 250 to 600 mg/60 kg body weight; and

[ornithine (in terms of free form)] preferably from 100 to 5,000 mg/60 kg body weight, more preferably from 250 to 3,000 mg/60 kg body weight, still more preferably from 400 to 2,000 mg/60 kg body weight, further preferably from 500 to 2,000 mg/60 kg body weight and still further preferably from 800 to 1,600 mg/60 kg body weight, or alternatively preferably from 250 to 800 mg/60 kg body weight and more preferably from 500 to 800 mg/60 kg body weight.

[74] The combination of catechins and ornithine according to [73], which the dosages of the catechins and ornithine are preferably administered once a day, or in divided doses twice or three or more times a day.

[75] A method for promoting ammonia metabolism, comprising administering effective amounts of catechins and ornithine to a subject in need thereof.

[76] A method for enhancing endurance, comprising administering effective amounts of catechins and ornithine to a subject in need thereof.

[77] A method for anti-fatigue, comprising administering effective amounts of catechins and ornithine to a subject in need thereof.

[78] A method for suppressing a reduction in blood glucose level by exercise, comprising administering effective amounts of catechins and ornithine to a subject in need thereof.

[79] A method for promoting recovery from reduced blood glucose level by exercise, comprising administering effective amounts of catechins and ornithine to a subject in need thereof.

[80] A method for suppressing a reduction in muscle glycogen by exercise, comprising administering effective amounts of catechins and ornithine to a subject in need thereof.

[81] A method for promoting recovery from reduced muscle glycogen by exercise, comprising administering effective amounts of catechins and ornithine to a subject in need thereof.

[82] A method for enhancing muscle endurance, comprising administering effective amounts of catechins and ornithine to a subject in need thereof.

[83] A method for preventing or ameliorating hyperammonemia, comprising administering effective amounts of catechins and ornithine to a subject in need thereof.
[84] A method for preventing or ameliorating hepatic encephalopathy, comprising administering effective amounts of catechins and ornithine to a subject in need thereof.
[85] A method for preventing or ameliorating chronic fatigue syndrome, comprising administering effective amounts of catechins and ornithine to a subject in need thereof.
[86] The method according to any one of [75] to [85], wherein the catechins is preferably at least one selected from the group consisting of catechin, gallocatechin, catechin gallate, gallocatechin gallate, epicatechin, epigallocatechin, epicatechin gallate and epigallocatechin gallate.
[87] The method according to any one of [75] to [86], wherein the mass ratio of the catechins to the ornithine is preferably from 1:0.1 to 1:10, more preferably from 1:0.5 to 1:10, still more preferably from 1:1 to 1:8, further preferably from 1:1 to 1:5 and still further preferably from 1:2 to 1:4.
[88] The method according to any one of [75] to [87], wherein the administration is oral administration.
[89] The method to any one of [75] to [88], wherein the daily dosages per adult of the catechins and ornithine are as follows:

[catechins] preferably from 100 to 3,000 mg/60 kg body weight, more preferably from 250 to 2,000 mg/60 kg body weight, still more preferably from 250 to 1,000 mg/60 kg body weight and further preferably from 250 to 600 mg/60 kg body weight; and

[ornithine (in terms of free form)] preferably from 100 to 5,000 mg/60 kg body weight, more preferably from 250 to 3,000 mg/60 kg body weight, still more preferably from 400 to 2,000 mg/60 kg body weight, further preferably from 500 to 2,000 mg/60 kg body weight and still further preferably from 800 to 1,600 mg/60 kg body weight, or alternatively preferably from 250 to 800 mg/60 kg body weight and more preferably from 500 to 800 mg/60 kg body weight.
[90] The method according to [89], which the dosages of the catechins and ornithine are preferably administered once a day, or in divided doses twice or three or more times a day.
[91] An ammonia metabolism promoting food, comprising catechins and ornithine as active ingredients.
[92] An endurance enhancing food, comprising catechins and ornithine as active ingredients.
[93] An anti-fatigue food, comprising catechins and ornithine as active ingredients.
[94] A food for suppressing a reduction in blood glucose level by exercise, comprising catechins and ornithine as active ingredients.
[95] A food for promoting recovery from reduced blood glucose level by exercise, comprising catechins and ornithine as active ingredients.
[96] A food for suppressing a reduction in muscle glycogen by exercise, comprising catechins and ornithine as active ingredients.
[97] A food for promoting recovery from reduced muscle glycogen by exercise, comprising catechins and ornithine as active ingredients.
[98] A muscle endurance enhancing food, comprising catechins and ornithine as active ingredients.
[99] A food for preventing or ameliorating hyperammonemia, comprising catechins and ornithine as active ingredients.
[100] A food for preventing or ameliorating hepatic encephalopathy, comprising catechins and ornithine as active ingredients.
[101] A food for preventing or ameliorating chronic fatigue syndrome, comprising catechins and ornithine as active ingredients.
[102] The food according to any one of [91] to [101], wherein the catechins is preferably at least one selected from the group consisting of catechin, gallocatechin, catechin gallate, gallocatechin gallate, epicatechin, epigallocatechin, epicatechin gallate and epigallocatechin gallate.
[103] The food according to any one of [91] to [102], wherein the food preferably comprises from 0.05 to 10% by mass, from 0.05 to 5% by mass, from 0.05 to 1% by mass, from 0.1 to 10% by mass, from 0.1 to 5% by mass, from 0.1 to 1% by mass, from 1 to 10% by mass or from 1 to 5% by mass of the catechins.
[104] The food according to [103], wherein the food preferably comprises from 0.15 to 30% by mass, from 0.15 to 20% by mass, from 0.15 to 15% by mass, from 0.15 to 5% by mass, from 0.15 to 3% by mass, from 0.3 to 30% by mass, from 0.3 to 20% by mass, from 0.3 to 15% by mass, from 0.3 to 5% by mass, from 0.3 to 3% by mass, from 3 to 30% by mass, from 3 to 20% by mass, from 3 to 15% by mass, from 3 to 5% by mass, from 5 to 30% by mass, from 5 to 20% by mass or from 5 to 15% by mass of the ornithine.
[105] The food according to any one of [91] to [104], wherein the mass ratio of the catechins to the ornithine is preferably from 1:0.1 to 1:10, more preferably from 1:0.5 to 1:10, still more preferably from 1:1 to 1:8, further preferably from 1:1 to 1:5 and still further preferably from 1:2 to 1:4.

EXAMPLES

Hereinafter, the present invention will be more specifically described with reference to examples. However, the technical scope of the present invention is not limited to these examples.

Reference Example 1 Preparation of Catechins-Containing Green Tea Extract

An amount of 1,000 g of a commercially available green tea extract ("POLYPHENON HG" from Mitsui Norin Co., Ltd.) was suspended in 9,000 g of a 95% by mass aqueous ethanol solution under stirring conditions at 25° C. and 200 rpm. To this were added 200 g of activated carbon ("KURARAY COAL GLC" from KURARAY CO., LTD.) and 500 g of acid clay ("MIZUKA-ACE #600" from MIZUSAWA INDUSTRIAL CHEMICALS, LTD.) and stirring was continued for about 10 minutes. Stirring was further continued at 25° C. for 30 minutes. Next, the suspension was filtered through No. 2 filter paper to remove activated carbon, acid clay and a precipitate, and the filtrate was then re-filtered through a 0.2 μm membrane filter. Ion exchanged water (200 g) was added to the filtrate, ethanol was distilled off at 40° C. and 3.3 kPa, and the residue was concentrated under reduced pressure. The concentrate (750 g) was charged into a stainless steel container, and the total amount was adjusted to 10,000 g with ion exchanged water, and 30 g of a 5% by mass aqueous sodium bicarbonate solution was added thereto to adjust the pH to 5.5. To the solution containing the resulting concentrate was added an enzyme liquid prepared by dissolving 2.7 g of Kikkoman tannase KTFH (industrial grade, 500 U/g or more) in 10.7 g of ion-exchanged water under stirring conditions at 22° C. and 150 rpm. After 30 minutes when the pH of the reaction liquid decreased to 4.24, the stainless steel container was immersed in a water bath at 95° C. and maintained at 90° C. for 10 minutes to completely inactivate the enzyme activity. Next, the reaction liquid was cooled to 25° C. and then concentrated to obtain a purified product of green tea extract. The resulting purified product of green tea extract had a content of (A) catechins of 14.9% by mass and a proportion of catechin gallates in the catechins was 45.3% by mass.

Example 1 Effects of Catechins and Ornithine on Ammonia Metabolism in Hepatocytes For hepatocytes, a hepatocyte culture kit P-2 (HPC03P-BAL, derived from male Balb/c mouse, 24 wells, 1×10$^5$ cells/well, from Cosmo Bio) was used. As catechins, the green tea extract (containing 14.9% by mass of catechins) prepared in Reference Example 1 was used. Hepatocytes were cultured at 37° C. for 20 hours, in a control medium, an ornithine-containing medium (1 mM ornithine hydrochloride-containing control medium), catechins-containing medium (0.001% by mass green tea extract-containing control medium), or an ornithine and catechins-containing medium (1 mM ornithine hydrochloride and 0.001% by mass green tea extract-containing control medium). As the control medium, a DMEM medium containing 5 mM ammonium chloride (high glucose, GlutaMAX added, penicillin/streptomycin added, pyruvic acid-free, phenol red-free, glutamine-free, FBS-free) was used. The culture supernatant after culturing was collected, and the ammonia contained therein was quantitatively determined using an ammonia assay kit (Abcam). A significant difference was tested between each quantitative value and that of the control group (Dunnett test, vs. control group, n=3).

The results of quantitative determination of ammonia are shown in FIG. 1. FIG. 1 shows that the ammonia concentration in the culture medium was statistically significantly reduced and ammonia metabolism was promoted in the ornithine hydrochloride and catechins-containing group, as compared to the control group.

Example 2 Effects of Catechins and Ornithine on Blood Ammonia Concentration and Fatigue Feeling During Exercise in Human (Method)
(Subject)

The subjects were 10 healthy adult males (26 to 36 years old). The physical strength was preliminarily measured for the subjects by bicycle pedaling exercise accompanied with the measurement of heart rate. One of ten subjects was excluded from the test due to the inability to reach the designated exercise intensity.

(Experimental Design)

The test was performed one week or more after the preliminary measurement of physical strength. In the test, the first exercise was performed on the first day, and for 2 weeks starting with that day, subjects were allowed to daily ingest 1 bottle of catechin drink (Healthya Water-Grapefruit Flavor 500 mL from Kao Corporation, containing 540 mg of catechins). The second exercise was performed the day after the day when the final bottle of catechin drink was ingested. The test was performed twice in total, and the two tests were separated from each other by a two or more week interval as a washout period.

(Exercise)

As exercise, bicycle pedaling exercise was performed. Exercise load was adjusted so that the exercise intensity reached an intensity of approximately 70% of the estimated maximum heart rate ([220−age]/min) of each subject in approximately 40 minutes from a starting 20 watt with a simple first-order increase.

(Test Materials)

One hour before the start of the first exercise, each subject ingested 500 mL of mineral water and a placebo supplement. One hour before the start of the second exercise, each subject ingested test materials: (i) 1 bottle of catechin drink and 16 tablets of placebo supplement; or (ii) 1 bottle of catechin drink and 12 tablets of ornithine supplement and 4 tablets of placebo supplement. Details of the test materials are as follows:

Catechin drink: Healthya Water-Grapefruit Flavor 500 mL (Kao Corporation), containing 540 mg of catechins per bottle;

Placebo supplement: PlacePlus (Placebo Pharmaceutical Co., Ltd.), amino acid-free; and Ornithine supplement: Ornithine (KYOWA HAKKO BIO CO., LTD.), containing 1,600 mg of ornithine in 12 tablets.

All subjects ingested (i) and (ii) once in the two tests, respectively. The test materials were provided by a single-blinded method.

(Measurement of Blood Ammonia Concentration)

For the first and second exercises in each test, blood was collected from the fingertip of each subject, immediately before exercise loading (at rest), and immediately, 5 minutes, 10 minutes, 15 minutes and 30 minutes after the completion of exercise. The blood ammonia concentration of the collected blood (whole blood) was measured with a blood ammonia measuring device (PocketChem BA PA-4140, ARKRAY, Inc.). For each time of blood collection in each subject, the measured value at the first exercise was subtracted from the measured value at the second exercise to obtain the transition value of blood ammonia concentration (Δ blood ammonia concentration). In addition, the area under the concentration curve (AUC) for the Δ blood ammonia concentration for the blood collection period (from immediately before exercise to 30 minutes after the completion of exercise) was determined for each subject.

The data from all subjects obtained in the two tests were divided into two groups of group (i) (test material (i)-administered group) and group (ii) (test material (ii)-administered group), depending on the type of test material ingested before the second exercise. For each group, the mean value of blood ammonia concentration, Δ blood ammonia concentration, and its AUC were determined (n=9 per group). In addition, for AUC, a significant difference was tested between both groups (t-test).

(Questionnaire about Degree of Fatigue)

After the second exercise in each test, the physical condition at the time of the second exercise (after ingestion of the test material) compared to the time of the first exercise (without ingestion of any test material) was asked from each subject by a questionnaire. The items of the questionnaire are as shown in FIG. 4. The answer to each item was selected from five scales from "1 (positive, good)" to "5 (negative, bad)" and "unclear".

[Results]
(Blood Ammonia Concentration)

The blood ammonia concentrations after the first exercise (without ingestion of any test material) and the second exercise (after ingestion of a test material) and Δ blood ammonia concentrations for groups (i) and (ii) are shown in FIGS. 2A to 2C, respectively. The data in FIGS. 2A to 2C represent the mean (±SE) for each of groups (i) and (ii) at the time of each blood collection. FIG. 3 shows AUC (mean±SE) of Δ blood ammonia concentrations for groups (i) and (ii). As shown in FIG. 2C and FIG. 3, the blood ammonia concentration is statistically significantly reduced in the combination group of catechins and ornithine (group (ii)), as compared to the group of catechins alone (group (i)). This indicates that the combined use of catechins and ornithine could suppress an increase in blood ammonia concentration during exercise.

(Degree of Fatigue)

The results of questionnaire about the degree of fatigue are shown in FIG. 4. In the combination group of catechins and ornithine (group (ii); Cat+O), more positive answers to the following items were obtained as compared to the group of catechins alone (group (i); Cat): "Were you able to move quickly?", "Were you able to easily exercise as a whole?", "Did you feel that you could continue to exercise for a long time?", "Do you feel stamina gained?", and "Has your post-exercise fatigue (physical fatigue) feeling changed?". This indicates that the combined use of catechins and ornithine reduced fatigue by exercise and enhanced endurance during exercise.

Example 3 Effects of Catechins and Ornithine on Blood Components and Muscle Endurance During Exercise in Human

[Method]
(Subject)

The subjects were 9 healthy adult males (27 to 39 years old). The physical strength was preliminarily measured for the subjects by bicycle pedaling exercise accompanied with the measurement of heart rate.

(Experimental Design)

The test was performed the day after the day when the physical strength was preliminarily measured. In the test, nine subjects were divided into two groups. One group was allowed to ingest, daily for 2 weeks, 1 bottle of control drink (placebo: Healthya Water-Grapefruit Flavor 500 mL, containing no catechins) and 12 tablets of placebo supplement (PlacePlus (Placebo Pharmaceutical Co., Ltd.)) as test products. The other group was allowed to ingest, daily for 2 weeks, 1 bottle of catechin drink (Healthya Water-Grapefruit Flavor 500 mL from Kao Corporation, containing 540 mg of catechins) and 12 tablet of ornithine supplement (ornithine (KYOWA HAKKO BIO CO., LTD.), containing 1600 mg of ornithine in 12 tablets)) as test products. The muscle endurance measuring test was performed the day after the last day of ingesting the test products. This test was performed twice in total in a crossover design, and the two tests were separated from each other by a six or more day interval as a washout period. The test materials were provided by a single-blinded method in which the contents of the test products were not revealed.

(Muscle Endurance Measuring Test)

Irregular bicycle pedaling exercise including continuous muscle strength measurements was performed according to the following procedure. The exercise intensity for each test participant was derived from the preliminary measurement.

1. Ingestion of test products: About one hour before the start of exercise load (warm-up), each subject was allowed to ingest the same test products as those ingested two weeks before the test.
2. Conditioning at rest: After change of clothes and warm-up exercise, each subject rested in the sitting position for 10 minutes.
3. Blood collection: Blood was collected from the fingertip.
4. Warm-up: Low-intensity (40 W, 50 rpm) exercise for 1 minute.
5. Rehearsal: Five revolutions of bicycle pedaling exercise at approximately 60% of the maximum muscle strength.
6. First continuous muscle strength measurement: Fifty rpm bicycle pedaling exercise was loaded by 16 revolutions at maximum muscle strength and the torque exerted at the time was measured as an exerted muscle strength.
7. Cool-down: Low-intensity (40 W, 50 rpm) exercise for 1 minute.
8. Break and blood collection: Each subject had a break in the same posture for 2 or 3 minutes, during which blood was collected from the fingertip.
9. Exercise: A 70% HRmax (not exceeding the Borg scale "heavy") intensity endurance exercise was loaded for 10 minutes.
10. Second continuous muscle strength measurement: Fifty rpm bicycle pedaling exercise was loaded by 16 revolutions at maximum muscle strength and the torque exerted at the time was measured as an exerted muscle strength.
11. Cool-down: Low-intensity (40 W, 50 rpm) exercise for 1 minute.
12. Blood collection: Immediately after the completion of the cool down, and 10 and 20 minutes after the muscle strength measurement, blood was collected from the fingertip.

All data from subjects obtained in the two tests performed in a crossover design were divided, depending on the type of test product which had been ingested before the test, into two groups: a control group (a control drink and placebo supplement-administered group) and a combination group of catechins and ornithine (a catechin drink and ornithine supplement-administered group).

(Measurement of Blood Ammonia Concentration and Blood Glucose Concentration)

For the blood (whole blood) of each subject collected in the muscle endurance measuring test, the blood ammonia concentration was measured with a blood ammonia measuring device (PocketChem BA PA-4140, ARKRAY, Inc.), and the blood glucose concentration was measured with ACCU-CHEC AVIVA (Roche). For each subject, the measured value at rest (before the first continuous muscle strength measurement) was subtracted from the measured value at each blood collection time to obtain the transition value of blood ammonia concentration (A blood ammonia concentration) and the transition value of blood glucose concentration (Δ blood glucose concentration). Comparison of the measured values between the groups was performed for each blood collection time point by a paired t-test.

(Muscle Endurance Measuring Test)

For each leg of each subject, the mean of the torque exerted in the 2nd to 15th revolutions at which the torque value was stabilized among the 16 revolutions of bicycle pedaling exercise in the continuous muscle strength measurement was determined, and it was defined as an exerted muscle strength. Comparison of the exerted muscle strength between the groups was performed with a total of 18 legs by nested ANOVA in which each subject was in a nested structure.

[Results]
(Blood Ammonia Concentration)

The mean (±SE) of the Δ blood ammonia concentration determined for the two tests is shown in FIG. 5A. The Δ blood ammonia concentration immediately after the first continuous muscle strength measurement was reduced in the combination group of catechins and ornithine than in the control group, and the increase in ammonia level accompanying exercise tended to be suppressed. Furthermore, at each time point after the completion of exercise (after the second continuous muscle strength measurement), the combination group of catechins and ornithine was higher in exercise intensity (momentum) than the control group, because of an increase in muscle strength in the second continuous muscle strength measurement (see FIG. 6), but the Δ blood ammonia concentration reduced. This indicates that the combined use of catechins and ornithine tended to suppress an increase in ammonia level accompanying exercise.

(Blood Glucose Concentration)

The mean (±SE) of the Δ blood glucose concentration determined for the two tests is shown in Figure SB. As compared to the control group, in the combination group of catechins and ornithine, the Δ blood glucose concentration tends to be reduced and suppressed immediately after the completion of exercise (the second continuous muscle strength measurement), and was significantly reduced and suppressed at the next two time points. These results indicate that in the combination group of catechins and ornithine, the reduction in blood glucose level during exercise was suppressed and the recovery of blood glucose level after exercise was also enhanced.

(Muscle Endurance)

The mean±SE of exerted muscle strength values of legs of all subjects measured in each of 2 tests is shown in FIG. 6. For the first continuous muscle strength measurement, no significant difference in the exerted muscle strength was found between the control group and the combination group of catechins and ornithine, but for the second continuous muscle strength measurement under fatigue condition, the exerted muscle strength value was significantly higher in the combination group of catechins and ornithine than in the control group. This indicates that the muscle endurance was enhanced in the combination group of catechins and ornithine.

Example 4 Effects of Catechins and Ornithine on Endurance

[Method]

The mice (male Balb/c, 8 weeks old; Orientalbio Co., Ltd.) were preliminarily bred for one week, and then divided into four groups so that the mean values of initial endurance were equal. Endurance was measured as a limit running time on a treadmill (8 degrees slope, 28 m/min) running. During the test period, mice were fed ad libitum with a test meal (AIN 76-based powder meal (10% lipid)) and water.

In the test, mice in each group were subjected to mild exercise running (treadmill, 8 degrees slope, 20 m/min, 30 minutes) four times a week for a total of 4 weeks. After 4 weeks, endurance (limit running time) of each individual was measured again on a treadmill (8 degrees slope, 28 m/min). One hour before each exercise running and endurance measurement, any one of the following test substances was intragastrically administered to the mice in each group using an oral probe. A significant difference was tested between the measured values of the limit running time of each test group and that of the control group (Dunnett test, vs. control, n=7 or 8).

After measurement of endurance (limit running time), a 2-day recovery period was provided, and each mouse was then forced to perform treadmill running (8 degrees slope, 25 m/min, 120 minutes). One hour before this running, the test substance was also intragastrically administered to the mice in each group. Immediately after exercise, mice were euthanized and dissected to collect quadriceps femoris muscles. The collected muscles were quickly frozen in liquid nitrogen after weight measurement, and stored at −80° C. until measurement. At a later date, for the stored quadriceps femoris muscles, the amount of glycogen was quantitatively determined using Glycogen Colorimetric Assay Kit II (BioVision), and the amount of protein was quantitatively determined using Pierce™ BCA protein Assay Kit (Thermo SCIENTIFIC). From each quantitative value, the amount of glycogen per mass of protein was quantitatively determined as a muscle glycogen amount. For quantitative values, a significant difference was tested between the groups (Tukey post hoc one way ANOVA, n=7 or 8).

(Test Substances)

Group 1 (control): Water

Group 2 (Cat): Tea catechins (0.2 g/kg body weight)

Group 3 (Orn): Tea catechins (0.2 g/kg body weight)+ornithine (ornithine hydrochloride 0.78 g/kg body weight (0.60 g/kg body weight in terms of ornithine))

Group 4 (Cat+Orn): Tea catechins (0.2 g/kg body weight)+ornithine (ornithine hydrochloride 0.78 g/kg body weight (0.60 g/kg body weight in terms of ornithine))

Tea catechins: Tea catechin formulation (POLYPHENON 70A from Mitsui Norin Co., Ltd.; catechins content: 77.44% (rates of gallates 95.1%); composition of catechins: EGCg 55.6%, EGC 2.1%, ECg 12.5%, EC 1.0%, GC 0.5%, GCg 4.9%, C 0.2%, Cg 0.6%; caffeine content: 0.195%, wherein % means % by mass)

Ornithine: Ornithine hydrochloride (KYOWA HAKKO BIO CO., LTD.)

Since 0.195% by mass of caffeine is contained in the tea catechin formulation, equal amounts of caffeine were administered to the group 1 (control) and the group 3 (Orn) (0.4 mg/kg body weight).

[Results]

The mean (±SE) of the limit running time on a treadmill of mice in each group is shown in FIG. 7. In the Cat+Orn group, a significant enhancement in endurance (limit running time) was observed relative to the control group. The mean (±SE) of muscle glycogen amount immediately after exercise is shown in FIG. 8. The muscle glycogen amount was significantly higher in the Cat+Orn group than any other groups.

The invention claimed is:

1. A method for enhancing endurance, comprising administering effective amounts of catechins and ornithine to a subject in need thereof.

2. The method of claim 1, wherein the endurance is muscle endurance.

3. The method according to claim 1, wherein the catechins to ornithine mass ratio is from 1:0.1 to 1:10.

* * * * *